US008329645B2

(12) United States Patent
Vaara et al.

(10) Patent No.: US 8,329,645 B2
(45) Date of Patent: *Dec. 11, 2012

(54) POLYMYXIN DERIVATIVES AND USES THEREOF

(75) Inventors: Martti Sakari Vaara, Helsinki (FI); Timo Ilmari Vaara, Helsinki (FI)

(73) Assignee: Northern Antibiotics Ltd., Helsinki (FI)

( * ) Notice: Subject to any disclaimer, the term of this patent is extended or adjusted under 35 U.S.C. 154(b) by 642 days.

This patent is subject to a terminal disclaimer.

(21) Appl. No.: 12/366,231

(22) Filed: Feb. 5, 2009

(65) Prior Publication Data

US 2009/0215677 A1 Aug. 27, 2009

Related U.S. Application Data

(60) Provisional application No. 61/065,073, filed on Feb. 8, 2008, provisional application No. 61/127,885, filed on May 16, 2008.

(51) Int. Cl.
*A61K 38/12* (2006.01)
(52) U.S. Cl. .......... 514/2.4; 514/2.8; 514/2.9; 514/21.1; 514/3.2; 530/319
(58) Field of Classification Search .................. None
See application file for complete search history.

(56) References Cited

U.S. PATENT DOCUMENTS

| | | | |
|---|---|---|---|
| 4,510,132 A | 4/1985 | Vaara | |
| 2004/0082505 A1 | 4/2004 | Ofek et al. | |
| 2006/0004185 A1 | 1/2006 | Leese et al. | |

FOREIGN PATENT DOCUMENTS

| | | |
|---|---|---|
| DE | 1906699 | 2/1970 |
| GB | 1323362 | 7/1973 |
| JP | 71-15630 | 4/1971 |
| JP | 72-51356 | 12/1982 |
| WO | 02/055543 A2 | 7/2002 |

OTHER PUBLICATIONS

CAS Accession No. 1978:406531, abstract for Zewail "Biologically active cyclopeptides: lysine analogs of polymyxin antibiotics M, D, E and B," Indian Journal of Chemistry, Section B: Organic Chemistry Including Medicinal Chemistry, 1977, 15B(2) 128-30.*
O'Dowd et al. ("Preparation of tetra-Boc-protected polymyxin B nonapeptide," Tetrahedron Letters, 2007, 48, 2003-2005).*
Kato, Toshiyuki et al., The Structure of Octapeptin D (Studies on Antibiotics from the Genus *Bacillus*. XXVIII), The Journal of Antibiotics, vol. 33(2):186-191 (1980).
Shoji, Jun'ichi et al., "Isolation of Octapeptin D (Studies on Antibiotics from the Genus *Bacillus*. XXVII)," The Journal of Antibiotics, vol. 33(2):182-185 (1980).
Chihara, Shiro et al., "Chemical Synthesis, Isolation and Characterization of α-N-Fattyacyl Colistin Nonapeptide with Special Reference to the Correlation between Antimicrobial Activity and Carbon Number of Fattyacyl Moiety," *Agr. Biol. Chem.*, vol. 38(3):521-529 (1974).
Chihara, Shiro et al., "Enzymatic Degradation of Colistin Isolation and Identification of α-N-Acyl α,γ-Diaminobutyric Acid and Colistin Nonapeptide," *Agr. Biol. Chem.*, vol. 37(11):2455-2463 (1973).
Clausell, A. et al., "Influence of polymyxins on the structural dynamics of *Escherichia coli* lipid membranes," *Talanta*, vol. 60:225-234 (2003).
de Visser, P.C. et al., "Solid-phase synthesis of polymyxin B1 and analogues via a safety-catch approach," *J. Peptide Res.*, vol. 61:298-306 (2003).
Kimura, Yukio et al., "Polymyxin B Octapeptide and Polymyxin B Heptapeptide are Potent Outer Membrane Permeability—Increasing Agents," *The Journal of Antibiotics*, vol. 45(5):742-749 (1992).
Kurihara, Tozaburo et al., "Studies on the Compounds related to Colistin. IX. On the Chemical Deacylation of Colistin and Colistin Derivatives," *Yakugaku Zasshi*, vol. 94(11):1491-1494 (1974).
Okimura, Keiko et al., "Chemical Conversion of Natural Polymyxin B and Colistin to Their *N*-Terminal Derivatives," *Bull. Chem. Soc. Jpn.*, vol. 80(3):543-552 (2007).
Potter, Ross et al., "Inhibition of foodborne bacteria by native and modified protamine: importance of electrostatic interactions," *International Journal of Food Microbiology*, vol. 103:23-34 (2005).
Sakura, Naoki et al., "The Contribution of the *N*-Terminal Structure of Polymyxin B Peptides to Antimicrobial and Lipopolysaccharide Binding Activity," *Bull. Chem. Soc. Jpn.*, vol. 77:1915-1924 (2004).
Srinivasa, B.R. et al., "Chemical Modification of Peptide Antibiotics: Part VI—Biological Activity of Derivatives of Polymyxin B," *Indian Journal of Biochemistry & Biophysics*, vol. 14:54-58 (1978).
Srinivasa, B.R. et al., "Deacylation of Polymyxin B by Hydrazine & Solvolysis," *Indian Journal of Biochemistry & Biophysics*, vol. 17:298-302 (1980).
Srinivasa, B.R. et al., "Essential Amino Groups of Polymyxin B," *Indian Journal of Biochemistry & Biophysics*, vol. 17:112-118 (1980).
Srinivasa, B.R. et al., "The Polymyxins," *Journal of Scientific and Industrial Research*, vol. 38:695-709 (1979).

(Continued)

*Primary Examiner* — Christina Bradley
(74) *Attorney, Agent, or Firm* — Lathrop & Gage LLP; Sean M. Coughlin

(57) ABSTRACT

The present invention relates to a polymyxin derivative wherein R1, R2 and R3 are optional and R1, R2, R3, R5, R8 and R9 are cationic or neutral amino acid residues selected so that the total number of positive charges at physiological pH is at least two but no more than three; and to a combination product comprising at least two such derivatives. The invention further relates to a method for treating, alleviating or ameliorating an infection in a subject, caused by a Gram-negative bacterium by administering a therapeutically effective amount of a derivative according to the present invention to said subject; to a method for sensitizing Gram-negative bacteria to an antibacterial agent by administering, simultaneously or sequentially in any order a therapeutically effective amount of said antibacterial agent and a derivative according to the present invention to said subject; to methods for developing novel antibiotics; for reducing the nephrotoxicity, for improving the pharmacokinetic properties of natural polymyxins and octapeptins; and for sensitizing clinically important bacteria to a host defense mechanism complement present in serum. Finally, the invention relates to a process for preparing such polymyxin derivatives.

16 Claims, No Drawings

OTHER PUBLICATIONS

Storm, Daniel R. et al., "Polymyxin and Related Peptide Antibiotics," *Annu. Rev. Biochem.*, vol. 46:723-763 (1977).

Teuber, Michael, "Preparation of biologically active mono-*N*-acetyl($^{14}$C)-derivatives of the membrane-specific polypeptide antibiotic polymyxin B," *Z. Naturforsch B.*, vol. 25(1):117 (1970).

Thomas, Celestine J. et al., "Kinetics of the interaction of endotoxin with polymyxin B and its analogs: a surface plasmon resonance analysis," *FEBS Letters*, vol. 445:420-424 (1999).

Tsubery, Haim et al., "N-terminal modifications of Polymyxin B nonapeptide and their effect on antibacterial activity," *Peptides*, vol. 22:1675-1681 (2001).

Tsubery, Haim et al., "Neopeptide Antibiotics That Function as Opsonins and Membrane-Permeabilizing Agents for Gram-Negative Bacteria," *Antimicrobial Agents and Chemotherapy*, vol. 49(8):3122-3128 (2005).

Tsubery, Haim et al., "Structure—Function Studies of Polymyxin B Nonapeptide: Implications to Sensitization of Gram-Negative Bacteria," *J. Med. Chem.*, vol. 43:3085-3092 (2000).

Tsubery, Haim et al., "The Functional Association of Polymyxin B with Bacterial Lipopolysaccharide Is Sterospecific: Studies on Polymyxin B Nonapeptide," *Biochemistry*, vol. 39(39):11837-11844 (2000).

Vaara, Martti, "Agents that Increase the Permeability of the Outer Membrane," *Microbiological Reviews*, vol. 56(3):395-411 (1992).

Vaara, Martti et al., "Group of Peptides That Act Synergistically with Hydrophobic Antibiotics against Gram-Negative Enteric Bacteria," *Antimicrobial Agents and Chemotherapy*, vol. 40(8):1801-1805 (1996).

Vaara, Martti, "Lipopolysaccharide and the Permeability of the Bacterial Outer Membrane," *Endotoxin in Health and Disease*, Chpt. 2, Helmut Brade Ed., pp. 31-38 (1999).

Vaara, Martti et al., "Sensitization of Gram-negative bacteria to antibiotics and complement by a nontoxic oligopeptide," *Nature*, vol. 303(5917):526-528 (1983).

Viljanen, Petri et al., "The Outer Membrane Permeability—Increasing Action of Deacylpolymyxins," *The Journal of Antibiotics*, vol. 44(5):517-523 (1991).

Weinstein, Jay et al., "Selective Chemical Modifications of Polymyxin B," *Bioorganic & Medicinal Chemistry Letters*, vol. 8:3391-3396 (1998).

Zewail, M.A., "Biologically Active Cyclopeptides: Lysine Analogs of Polymyxins Antibiotics M, D, E & B," *Indianl Journal of Chemistry*, vol. 15B:128-130 (1977).

European Office Action for Application No. 07803704.1, dated Jul. 21, 2009.

International Search Report for Application No. PCT/FI2007/050441, dated Nov. 22, 2007.

International Search Report for Application No. PCT/FI2009/050093, dated Jul. 24, 2009.

Clausell, Adriá et al., "Gram-Negative Outer and Inner Membrane Models: Insertion of the Cyclic Cationic Lipopeptides," *J. Phys. Chem. B.*, vol. 111:551-563 (2007).

Li, Jian et al., "A simple method for the assay of colistin in human plasma, using pre-column derivatization with 9-fluorenylmethyl chloroformate in solid-phase extraction cartridges and reversed-phase high-performance liquid chromatography," *Journal of Chromatography B*, vol. 761:167-175 (2001).

Li, Jian et al., "Pharmacokinetics of colistin methanesulphonate and colistin in rats following an intravenous dose of colistin methanesulphonate," *Journal of Antimicrobial Chemotherapy*, vol. 53:837-840 (2004).

Li, Jian et al., "Use of High-Performance Liquid Chromatography to Study the Pharmacokinetics of Colistin Sulfate in Rats following Intravenous Administration," *Antimicrobial Agents and Chemotherapy*, vol. 47(5):1766-1770 (2003).

Nagai, Junya et al. "Inhibition of gentamicin binding to rat renal brush-border membrane by megalin ligands and basic peptides," *Journal of Controlled Release*, vol. 112:43-50 (2006).

Nikaido, Hiroshi et al., "Molecular Basis of Bacterial Outer Membrane Permeability," *Microbiological Reviews*, vol. 49(1):1-32 (1985).

Nikaido, Hiroshi et al., "Molecular Basis of Bacterial Outer Membrane Permeability Revisited," *Microbiological Reviews*, vol. 67(4):593-656 (2003).

Rose, Frank et al., "Targeting Lipopolysaccharides by the Nontoxic Polymyxin B Nonapeptide Sensitizes Resistant *Escherichia coli* to the Bactericidal Effect of Human Neutrophils," *The Journal of Infectious Diseases*, vol. 182:191-199 (2000).

Tsubery, Haim et al., "Modulation of the Hydrophobic Domain of Polymyxin B Nonapeptide: Effect on Outer-Membrane Permeabilization and Lipopolysaccharide Neutralization," *Molecular Pharmacology*, vol. 62(5):1036-1042 (2002).

Vaara, Martti et al., "An Outer Membrane-disorganizing Peptide PMBN Sensitizes *E. coli* Strains to Serum Bactericidal Action," *The Journal of Immunology*, vol. 132(5):2582-2589 (1984).

Vaara, Martti et al., "Antibiotic-Supersusceptible Mutants of *Escherichia coli* and *Salmonella typhimurium*," *Antimicrobial Agents and Chemotherapy*, vol. 37(11):2255-2260 (1993).

Vaara, Martti et al., "Polycations as Outer Membrane-Disorganizing Agents," *Antimicrobial Agents and Chemotherapy*, vol. 24(1):114-122 (1983).

Vaara, Martti et al., "Polycations Sensitize Enteric Bacteria to Antibiotics," *Antimicrobial Agents and Chemotherapy*, vol. 24(1):107-113 (1983).

Ali, Feda' Emad Atta et al., "Pharmacokinetics of novel antimicrobial cationic peptides NAB 7061 and NAB 739 in rats following intravenous administration," *Journal of Antimicrobial Chemotherapy*, vol. 64:1067-1070 (2009).

* cited by examiner

POLYMYXIN DERIVATIVES AND USES THEREOF

RELATED APPLICATIONS

This application claims priority to U.S. Provisional Patent Application Ser. No. 61/065,073, filed Feb. 8, 2008, and U.S. Provisional Patent Application Ser. No. 61/127,885, filed May 16, 2008. This application is related to U.S. patent application Ser. No. 11/891,629, filed on Aug. 10, 2007, which claims priority to U.S. Provisional Patent Application Ser. No. 60/837,426, filed Aug. 11, 2006. The entire contents of each of these applications are hereby incorporated herein by reference in their entirety.

TECHNICAL FIELD

The present invention relates to polymyxin derivatives and to uses thereof in the treatment of infections caused by Gram-negative bacteria. The polymyxin derivatives may have antibacterial effects or may sensitize bacteria to enhance the effects of other antibacterial agents.

BACKGROUND

Sepsis kills more than 215,000 Americans each year. It is estimated that 750,000 Americans are infected with severe sepsis and 29% of them die from it each year. Sepsis deaths make 9% of all death cases in the U.S. Sepsis kills as many Americans as myocardial infections, even more than traffic accidents.

Two to three million Americans acquire a hospital infection each year and 10% of these infections progress to sepsis. More than 90,000 of these patients die from sepsis infected in hospitals.

Severe sepsis and septic shock (severe sepsis combined with low blood pressure) took up to 135,000 lives each year in the intensive care units (ICU) in the European Union according to the OECD Health Report of 2000. In Britain, 5,000 out of 100,000 patients who acquired a hospital infection die from sepsis every year in acute care hospitals belonging to the NHS organisation.

The death toll has increased year after year due to the fact that the number of patients predisposed to sepsis, such as the elderly, premature neonates, and cancer patients, has increased, not least because many serious illnesses are more treatable than before. Also the use of invasive medical devices and aggressive procedures has increased.

Gram-negative bacteria cause more than 40% of all septicemic infections and many of the Gram-negative bacteria are extremely multiresistant. Gram-negative bacteria provide a harder challenge in therapy than Gram-positives, as they possess a unique structure, the outer membrane, as their outermost structure. Lipopolysaccharide molecules located on the outer membrane inhibit the diffusion of many antibacterial agents deeper into the cell, where their ultimate targets are located. More than 95% of the novel antibacterial agents isolated from nature or chemically synthesized in 1972-1991 lacked activity against Gram-negatives (Vaara 1993).

Polymyxins are a group of closely related antibiotic substances produced by strains of *Paenibacillus polymyxa* and related organisms. These cationic drugs are relatively simple peptides with molecular weights of about 1000. Polymyxins, such as polymyxin B, are decapeptide antibiotics, i.e., they are made of ten (10) aminoacyl residues. They are bactericidal and especially effective against Gram-negative bacteria such as *Escherichia coli* and other species of Enterobacteriaceae, *Pseudomonas, Acinetobacter baumannii*, and others. However, polymyxins have severe adverse effects, including nephrotoxicity and neurotoxicity. These drugs thus have limited use as therapeutic agents because of high systemic toxicity.

Polymyxins have been used in the therapy of serious infections caused by those bacteria, but because of the toxicity, their use was largely abandoned in the 70's when newer, better tolerated antibiotics were developed. The recent emergence of multiresistant strains of Gram-negative bacteria has necessitated the therapeutic use of polymyxins as the last resort, in spite of their toxicity, and as many of the less toxic antibiotics have already lost their effectiveness against particular strains of the said bacteria, the use of polymyxins has again increased.

Accordingly, polymyxins have now been recalled to the therapeutic arsenal, although, due to their toxicity, on a very limited scale. Their systemic (i.e., non-topical) use is, however, largely restricted to the therapy of life-threatening infections caused by multiply resistant strains of *Ps. aeruginosa* and *A. baumannii* as well as by carbapenem-resistant enteric bacteria.

Polymyxins consist of a cyclic heptapeptide part and a linear part consisting of a tripeptide portion and a hydrophobic fatty acid tail linked to the α-amino group of the N-terminal amino acid residue of the tripeptide and may be represented by the general formula:

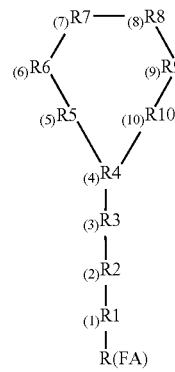

wherein R1-R3 represent the tripeptide side chain portion; R4-R10 the heptapeptide ring portion and R(FA) represents the hydrophobic fatty acid tail linked to the α-amino group of the N-terminal amino acid residue of the tripeptide.

The polymyxin group includes the following polymyxins: A1, A2, B1-B6, IL-polymyxin B1, C, D1, D2, E1, E2, F, K1, K2, M, P1, P2, S, and T (Storm et al. 1977; Srinivasa and Ramachandran 1979). All polymyxins are polycationic and possess five (5) positive charges, with the exception of polymyxin D, F, and S which possess four (4) positive charges. It should be noted that modified polymyxins that lack the fatty acid part R(FA) but carry R1-R10 have one additional positive charge when compared to the natural polymyxins they derived from, due to the free α-amino group in the N-terminus of the derivative. Accordingly, for example, such a derivative of polymyxin B or polymyxin E carries six (6) positive charges in total.

The clinically used polymyxin B and polymyxin E differ from each other only in the residue R6, which is D-phenylalanyl residue in polymyxin B and D-leucyl residue in polymyxin E.

Also circulin A and B are classified as polymyxins (Storm et al. 1977). They differ from other polymyxins only in carrying isoleucyl residue in the position R7 whereas other polymyxins have either threonyl or leucyl residue in the said position. For an overview of the structures of some polymyxins, see Table 1.

certain limits they have preserved their biological activity. The modifications comprise but are not limited to those in the side chain, as well as molecules in which an inherent hydrophobic amino acid residue (such as DPhe or Leu) has been replaced with another hydrophobic amino acid residue or in which the cationic Dab has been replaced with another cat-

TABLE 1

The structure of selected polymyxins and octapeptin as well as selected derivatives thereof

| Compound | R(FA) | R1 | R2 | R3 | R4 | R5 | R6 | R7 | R8 | R9 | R10 |
|---|---|---|---|---|---|---|---|---|---|---|---|
| Polymyxin B | MO(H)A- | Dab- | Thr- | Dab- | *Dab- | Dab- | D-Phe | Leu- | Dab | Dab | *Thr |
| Colistin (polymyxin E) | MO(H)A- | Dab- | Thr- | Dab- | *Dab- | Dab- | D-Leu | Leu- | Dab | Dab | *Thr |
| Colistin sulphomethate | MO(H)A- | sm-Dab | Thr- | sm-Dab | *Dab- | Sm-Dab | D-Leu | Leu- | sm--Dab | sm--Dab | *Thr |
| Polymyxin A | MO(H)A- | Dab- | Thr- | D Dab- | *Dab- | Dab- | D-Leu | Thr- | Dab | Dab | *Thr |
| Polymyxin M | MOA | Dab- | Thr- | Dab- | *Dab- | Dab- | D-Leu | Thr- | Dab | Dab | *Thr |
| Polymyxin D | MO(H)A- | Dab- | Thr- | D Ser- | *Dab- | Dab- | D-Leu | Thr- | Dab | Dab | *Thr |
| Circulin A | MOA | Dab- | Thr- | Dab- | *Dab- | Dab- | D-Leu | Ile- | Dab | Dab | *Thr |
| Octapeptin A | OHMDA | — | | Dab- | *Dab- | Dab- | D-Leu | Leu- | Dab | Dab | *Leu |
| Deacylcolistin (DAC) | | Dab- | Thr- | Dab- | *Dab- | Dab- | D-Leu | Leu- | Dab | Dab | *Thr |
| Polymyxin E nonapeptide (PMEN) | | | Thr- | Dab- | *Dab- | Dab- | D-Leu | Leu- | Dab | Dab | *Thr |
| Deacylpolymyxin B (DAPB) | | Dab- | Thr- | Dab- | *Dab- | Dab- | D-Phe | Leu- | Dab | Dab | *Thr |
| Polymyxin B nonapeptide (PMBN) | | | Thr- | Dab- | *Dab- | Dab- | D-Phe | Leu- | Dab | Dab | *Thr |
| Polymyxin B octapeptide (PMBO) | | | | Dab- | *Dab- | Dab- | D-Phe | Leu- | Dab | Dab | *Thr |
| Polymyxin B heptapeptide (PMHP) | | | | | *Dab- | Dab- | D-Phe | Leu- | Dab | Dab | *Thr |

Polymyxin B is represented by the following formula:

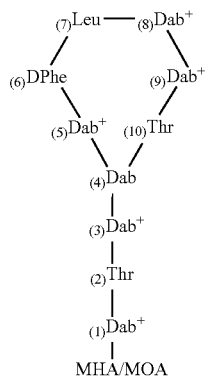

Commercially available polymyxin B is a mixture, where R-FA is predominantly 6-methyloctanoyl (6-MOA, in polymyxin B1) but may also be a related fatty acyl such as 6-methylheptanoyl (6-MHA, in polymyxin B2), octanoyl (in polymyxin B3), or heptanoyl (polymyxin B4) (Sakura et al. 2004). All these variants are equally potent against Gram-negatives such as *E. coli* (Sakura et al. 2004). Quite analogously, in polymyxin E1 (colistin A) and in circulin A the R-FA is 6-MOA and in polymyxin E2 (colistin B) and in circulin B the R-FA is 6-MHA. Numerous researchers have attached various hydrophobic moieties including various fatty acyl residues to the N-terminus of polymyxin derivatives and analogues and have shown that the resulting derivatives have potent antibacterial activity (Chihara et al. 1973, Sakura et al. 2004 and in US patent publication 2006004185. Even the derivative that carries the bulky hydrophobic 9-fluorenylmethoxycarbonyl residue as the R-FA is almost as potent as polymyxin B in inhibiting the growth of *E. coli* and other Gram-negative bacteria (Tsubery et al. 2001).

For biological activity the heptapeptide ring structure is essential (Storm et al. 1997). A derivative with an octapeptide ring is significantly less active as an antibiotic.

Multiple modifications of polymyxins and multiple polymyxin-like synthetic molecules have been made, and with certain limits they have preserved their biological activity.

ionic amino acyl residue, such as Lys, Arg, or ornithine residue (Storm et al. 1997, Tsubery et al. 2000a, Tsubery et al. 2002, US patent publication 2004082505, Sakura et al. 2004, US patent publication 2006004185).

Other modifications that result in microbiologically at least partially active compounds comprise but are not limited to alkanoyl esters where the OH-groups of the threonyl residues form esters with alkanoyls such as propionyl and butyryl (U.S. Pat. No. 3,450,687).

Octapeptins are otherwise identical to polymyxins but have a covalent bond instead of the residues R1-R2 (Table 1). In this invention, the R positions are numbered according to those in the natural polymyxins and thus the only amino acyl residue in the side chain of octapeptins is defined as R3. Accordingly, octapeptins are octapeptides whereas all natural polymyxins are decapeptides, and they possess only four (4) positive charges. The R-FA residues among various octapeptins (A1, A2, A3, B1, B2, B3, C1) include the following: 3-OH-8-methyldecanoic acid, 3-OH-8-methylnonanoic acid, and β-OH-6-methyloctanoic acid. Derivatives that possess a fatty acyl residue with 6 to 18 carbon atoms have a potent antibacterial activity against *E. coli* (Storm et al. 1977).

The first target of polymyxins in Gram-negative bacteria is their outer membrane (OM) that is an effective permeability barrier against many noxious agents including large (Mw more than 700 d) antibiotics as well as hydrophobic antibiotics. By binding to the lipopolysaccharide (LPS) molecules exposed on the outer surface of the OM, polymyxins damage the structure and function of the OM and, as a result, permeabilize (i.e., make permeable) the OM to polymyxin itself, as well as to many other noxious agents (Nikaido and Vaara 1985, Vaara 1992, Nikaido 2003). The final and lethal target (the bactericidal target) of polymyxins is believed to be the cytoplasmic membrane (the inner membrane) of bacteria.

Numerous efforts have been made to reduce the toxicity of polymyxins. The treatment of polymyxin E (colistin) with formaldehyde and sodium bisulfite yields colistin sulphomethate, in which the free amino groups of the five diaminobutyric acid residues have partially been substituted by sulphomethyl groups (Table 1). The preparations consist of undefined mixtures of the mono-, di-, tri-, tetra-, and pentasubstituted compounds. The sulphomethylated preparations, when freshly dissolved in water, initially lack both the antibacterial activity and toxicity of the parent molecule, but when the compounds start decomposing in the solution, in the blood or in the tissues to yield less substituted derivatives and free colistin, both the antibacterial activity and the toxicity are partially brought back. Furthermore, the degree of initial sulphomethylation apparently varies between the commercially available pharmaceutical preparations. Many other ways to block all the free amino groups have been published. Examples comprise but are not limited to the formation of unstable Shiff bases with amino acids (Storm et al. 1977).

Polymyxin E nonapeptide (PMEN, colistin nonapeptide, Table 1), obtained by treating polymyxin E enzymatically and lacking the R-FA and R1, was shown in 1973 to be less toxic than the parent compound in acute toxicity assay (immediate death presumably due to direct neuromuscular blockade) in mice (Chihara et al. 1973). However, it also lacked the antibacterial activity, as measured as its ability to inhibit bacterial growth (Chirara et al. 1973). The role of the linear part may contribute to the antibacterial activity of the polymyxins.

Vaara and Vaara, on the other hand, showed that polymyxin B nonapeptide (PMBN, Table 1) retains the ability to permeabilize the OM of Gram-negative bacteria (Vaara and Vaara 1983a,b,c; U.S. Pat. No. 4,510,132; Vaara 1992). Accordingly, even though it lacks the direct antibacterial activity (i.e., the ability to inhibit bacterial growth), it is able to sensitize (i.e., make sensitive or, as also termed, make susceptible) the bacteria to many antibacterial agents such as hydrophobic antibiotics as well as large antibiotics and some other noxious agents.

PMBN also sensitizes bacteria to the bactericidal activity of the human complement system, present in fresh human serum as a first-line defence system against invaders (Vaara and Vaara 1983a, Vaara et al. 1984, Vaara 1992). Furthermore, it sensitizes the bacteria to the joint bactericidal activity of serum complement and human polymorphonuclear white cells (Rose et al. 1999).

PMBN resembles PMEN in being less toxic in the acute toxicity assay in mice than unmodified polymyxins. In further toxicological assays, several criteria proved PBMN to be less toxic than its parent compound, but this polymyxin derivative was still judged to be too nephrotoxic for clinical use (Vaara 1992).

PMBN carries five (5) positive charges. Subsequent studies revealed, quite expectedly, that PMEN, also carrying five (5) positive charges as well as deacylpolymyxin B and deacylpolymyxin E, both carrying six (6) positive charges are potent agents to sensitize bacteria to other antibiotics (Vilijanen et al. 1991, Vaara 1992). In addition, it has been shown that a structurally further reduced derivative polymyxin B octapeptide (PMBO) retains a very effective permeabilizing activity while polymyxin B heptapeptide (PMBH) is less active (Kimura et al. 1992). PMBN, PMEN and PMBO have five (5) positive charges while PMBH has only four (4) positive charges. This difference may explain the weaker activity of PMBH.

The group of Ofek, Tsubery and Friedkin recently described polymyxin-like peptides that were linked to chemotactic peptides, such as fMLF, that attract polymorphonuclear leucocytes (US patent publication 2004082505, Tsubery et al. 2005). They described peptides fMLF-PMBN, MLF-PMBN, fMLF-PMEN, fMLF-PMBO and MLF-PMBO, all carrying four (4) positive charges, that sensitize Gram-negative bacteria to antibiotics, even though no comparative studies with increasing concentrations of the compounds were published (Tsubery et al. 2005).

In order to study the structures and functional properties of polymyxins, a few works have disclosed, among other compounds, polymyxin derivatives having less than four (4) positive charges.

Teuber (1970) has described the treatment of polymyxin B with acetic anhydride that yields a preparation containing polymyxin B as well as its mono-, di-, tri-, tetra-, and penta-N-acetylated forms. Teuber also separated each group and nonquantitatively reported using an agar diffusion assay that penta-acetylated and tetra-acetylated forms lacked the ability to halt the growth of *Salmonella typhimurium*, whereas di- and monoacetylated forms did have such ability. Triacetylated form had some ability.

Srinivasa and Ramachandran (1978) isolated partially formylated polymyxin B derivatives and showed that a diformyl derivative as well as a triformyl derivative inhibited the growth of *Pseudomonas aeruginosa*. They did not disclose the compounds' ability to sensitize bacteria to antibiotics. Furthermore, in 1980 they showed that the free amino groups of triformylpolymyxin B in residues R1 and R3, as well as the free amino groups of diformylpolymyxin B in residues R1, R3, and R5 are essential while the free amino groups in R8 and R9 are not essential for the growth inhibition (Srinivasa and Ramachandran, 1980a).

A shortened polymyxin B derivative octanoyl polymyxin B heptapeptide has been disclosed by Sakura et al. (2004). The attachment of the octanoyl residue to the N-terminus of the residue R4 of the polymyxin B heptapeptide results in a compound having only three (3) positive charges. Sakura et al. found that octanoyl polymyxin B heptapeptide inhibits the growth of bacteria only at a very high concentration (128 µg/ml), whereas the other derivatives such as octanoyl polymyxin B octapeptide and octanoyl polymyxin B nonapeptide, both having four charges (4) were very potent agents to inhibit bacterial growth.

US patent publication 2006004185 recently disclosed certain polymyxin derivatives and intermediates that can be used to synthesize new peptide antibiotics. The antibacterial compounds described possessed four (4) or five (5) positive charges.

Furthermore, closely related polymyxin B and polymyxin $B_1$ compounds have also been disclosed by Okimura et al. (2007) and de Visser et al. (2003). Okimura et al. have studied the chemical conversion of natural polymyxin B and their N-terminal derivatives and de Visser et al. have studied solid-phase synthesis of polymyxin $B_1$ and analogues via a safety-catch approach. The antibacterial compounds described in these works possessed four (4) or five (5) positive charges.

There is still an urgent need for effective treatments for bacterial infections, in particular for the infections caused by multiresistant Gram-negative bacteria.

SUMMARY

The present invention relates to novel polymyxin derivatives. In one embodiment, the derivatives are of the formula (I):

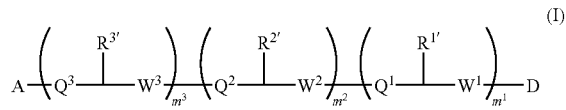

wherein.
A is a polymyxin ring moiety;
D is a terminal moiety;
$m^1$, $m^2$, and $m^3$ are each independently 0 or 1;

$Q^1$, $Q^2$, and $Q^3$ are each independently $CH_2$, C═O, or C═S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof, wherein said derivative has at least two but no more than three positive charges at physiological pH, provided that when (1) A is a polymyxin B ring moiety, and $m^1$, $m^2$, and $m^3$ are each 0, then D is not octanoyl; (2) when D is (S)-6-methyloctanoyl, hexanoyl, myristoyl, octanoyl or octanoyl-Dab, then $R^3$ is not the side chain of Dab; or (3) provided that said derivative is not 8,9-diformylated polymyxin B.

In another embodiment, the invention pertains, at least in part, to polymyxin derivatives of formula (II):

(II)

wherein:

A is a polymyxin ring moiety;

D is a hydrophobic oligopeptide, $R^{12}$—C(═O) or $R^{12}$—C(═S);

$m^1$, $m^2$, and $m^3$ are each independently 0 or 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^{12}$ is $C_5$-$C_{17}$ alkyl, $C_5$-$C_{17}$ alkenyl, $C_5$-$C_{17}$ aryl, $C_5$-$C_{17}$ arylalkyl or $C_5$-$C_{17}$ alkynyl, and pharmaceutically acceptable prodrugs and salts thereof, wherein said derivative has at least two and no more than three positive charges at physiological pH, and provided (1) when A is a polymyxin B ring moiety, and $m^1$, $m^2$, and $m^3$ are each 0, then D is not octanoyl; (2) when D is (S)-6-methyloctanoyl, hexanoyl, myristoyl, octanoyl or octanoyl-Dab, then $R^3$ is not the side chain of Dab; or (3) that said derivative is not 8,9-diformylated polymyxin B.

In another embodiment, the invention also pertains, at least in part, to polymyxin derivatives of formula (III):

(III)

wherein:

A is a polymyxin B or polymyxin E ring moiety;

D is $R^{12}$—C(═O) or $R^{12}$—C(═S);

$m^1$ is 0 or 1;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl, wherein at least one of $R^{2'}$ and $R^{3'}$ comprise a carbamyl, hydroxyl or carboxylate group; and $R^{12}$ is $C_5$-$C_{17}$ alkyl, and pharmaceutically acceptable prodrugs and salts thereof, wherein said derivative has at least two but no more than three positive charges at physiological pH, and provided (1) when D is (S)-6-methyloctanoyl, hexanoyl, myristoyl, octanoyl or octanoyl-Dab, then $R^3$ is not the side chain of Dab; or (2) said derivative is not 8,9-diformylated polymyxin B.

In another embodiment, the invention also pertains, at least in part, to polymyxin derivatives of formula (IV):

(IV)

wherein:

A is a polymyxin B or polymyxin E ring moiety;

$m^1$ is 0 or 1;

$L^1$, $L^2$ and $L^3$ are each independently $C_1$-$C_3$ alkyl or a covalent bond;

$M^1$, $M^2$ and $M^3$ are each independently H, $NH_2$, C(═O)$NH_2$, C(═O)OH, or —OH;

$R^{12}$ is $C_5$-$C_{17}$ alkyl, and pharmaceutically acceptable prodrugs and salts thereof, and wherein said derivative has at least two but no more than three positive charges at physiological pH, and provided (1) when D is (S)-6-methyloctanoyl, hexanoyl, myristoyl, octanoyl or octanoyl-Dab, then $R^3$ is not the side chain of Dab; or (2) said derivative is not 8,9-diformylated polymyxin B.

In yet another embodiment, the invention also pertains to polymyxin derivatives of the general formula (V), (V)

wherein R4 is an amino acid residue comprising a functional side chain able to cyclicize the molecule;

R6 is an optionally substituted hydrophobic amino acid residue;

R7 is an optionally substituted hydrophobic residue;

R10 is Leu or any non-hydrophobic amino acid residue; and wherein R1, R2, and R3 are optional; and wherein R1, R2, R3, R5, R8 and R9 are amino acid residues selected so that the total number of positive charges at physiological pH is at least two and no more than three; and wherein R(FA) is an optionally substituted alkanoyl or alkyl residue or a hydrophobic oligopeptide;

or a pharmaceutically acceptable prodrug or salt thereof, provided that (1) when R8 and R9 are formylated, R(FA)-R1-R2-R3 does not constitute a native polymyxin B side chain;

(2) provided that when R4-R10 is a polymyxin B ring moiety and R1, R2, and R3 are each absent, then R(FA) is not octanoyl, or (3) when R(FA) is (S)-6-methyloctanoyl, hexanoyl, myristoyl, octanoyl or octanoyl-Dab, then $R^3$ is not the side chain of Dab.

The present invention relates to a polymyxin derivative wherein the total number of positive charges at physiological pH is at least two but no more than three, with the proviso that R8 and R9 are not both formylated when R(FA)-R1-R2-R3 constitutes the native polymyxin B side chain; and R4 is not directly linked to octanoyl residue when R4-R10 constitutes a native polymyxin B ring structure.

The invention also relates to a combination product comprising two or more of the derivatives according to the present invention, and to a pharmaceutical composition comprising such derivative(s) or a combination thereof and pharmaceutically acceptable carriers and excipients.

Furthermore, the present invention relates to a method for treating, alleviating or ameliorating an infection in an individual, e.g., a mammal, e.g., a human, caused by a Gram-negative bacterium, comprising administering a therapeutically effective amount of a derivative or a combination according to the present invention to said individual, wherein said bacterium may be selected from the group consisting of: *Escherichia coli, Klebsiella pneumoniae, Klebsiella oxytoca, Enterobacter cloacae, Citrobacter freundii, Pseudomonas aeruginosa*, and *Acinetobacter baumannii*.

In another embodiment, the present invention relates to a method for sensitizing Gram-negative bacteria to an antibacterial agent, comprising administering, simultaneously or sequentially in any order, a therapeutically effective amount of said antibacterial agent and a derivative according to the present invention, wherein said antibacterial agent may be selected from the group consisting of clarithromycin, azithromycin, erythromycin and other macrolides, ketolides, clindamycin and other lincosamines, streptogramins, rifampin, rifabutin, rifalazile and other rifamycins, fusidic acid, mupirocin, oxazolidinones, vancomycin, dalbavancin, telavancin, oritavancin and other glycopeptide antibiotics, fluoroquinolones, bacitracin, tetracycline derivatives, betalactam antibiotics, novobiocin, pleuromutilins, folate synthesis inhibitors, deformylase inhibitors, and bacterial efflux pump inhibitors.

Also provided are methods for developing novel antibiotics; for reducing the toxicity of natural polymyxins, octapeptins and their derivatives; for improving the pharmacokinetic properties of natural polymyxins, octapeptins and their derivatives; and for sensitizing clinically important Gram-negative bacteria to a host defense mechanism complement present in the serum.

The present invention also provides uses of a polymyxin derivative according to the present invention in the manufacture of medicament for treating infections caused by Gram-negative bacteria, such e.g., *Escherichia coli, Klebsiella pneumoniae, Klebsiella oxytoca, Enterobacter cloacae, Citrobacter freundii, Pseudomonas auruginosa* and *Acinetobacter baumannii*; for the manufacture of a medicament for sensitizing Gram-negative bacteria against antibacterial agents; and for sensitizing Gram-negative bacteria to a host defense mechanism complement present in the serum.

Finally, the present invention relates to a process for preparing a polymyxin derivative according to the present invention, comprising modifying a natural or synthetic polymyxin or octapeptin compound or a derivative thereof having 4 to 6 positively charged residues by replacing 1 to 4 of said residues by neutral residues or a covalent bond, or by converting 1 to 4 of said residues into neutral residues in order to obtain a polymyxin derivative of formula (I) having 2 or 3 positively charged residues.

DEFINITIONS

"Physiological pH" as used herein refers to a pH value of more than 7.0 and below 7.6, such as a pH value in the range of from 7.1 to 7.5, for example in the range of from 7.2 to 7.4.

"Positive charge" as used herein denote positive charges at the above-defined physiological pH.

"Cationic" molecule as used herein refers to a molecule that contains one or more positive charges.

"Amino acid residue" as used herein refers to any natural, non-natural or modified amino acid residue, either in L- or D-configuration.

"Equivalent residues" as used herein, is intended to include obvious modifications to e.g., amino acids, resulting in non-natural amino acids or derivatives thereof, but retaining the structural and/or functional capacity of the replaced residue.

"Natural polymyxin(s)" as used herein, refers to polymyxins and circulins.

"Polymyxin derivative" refers, for the purpose of this invention, to synthetic or semisynthetic derivatives of natural polymyxins or octapeptins, which have a cyclic heptapeptide (or heptapeptide ring) portion R4-R10 and a side chain linked to the N-terminal aminoacyl residue R4. The side chain may consist of an R(FA)-triaminoacyl(R1-R3), an R(FA)-diaminoacyl(R2-R3), an R(FA)-monoamino-acyl(R3), or of R(FA) alone. In one embodiment of the invention, the derivatives of the invention do not include 8,9-diformylated polymyxin B. This compound comprises native polymyxin B with two formyl groups on the R8 and R9 residues as shown in Formula (V).

"R(FA)" or "fatty acid tail" as used herein refers to the fatty acid part, i.e., the alkanoyl part of the polymyxin structure, linked to the N-terminal amino acid residue of the linear peptide part (side chain) of the polymyxin or, in the absence of the linear peptide part, to the amino acid residue R4 (the amino acid in 4-position of the cyclic peptide part of the polymyxin). Furthermore, for the purpose of the present invention, R(FA) may also be a related hydrophobic group, such as alkyl. In certain embodiments of the invention, the fatty acid tail may, in certain instances, be a terminal moiety selected from the group consisting of a hydrophobic oligopeptide, $R^{12}$—(C=O); $R^{12}$—$SO_2$—; $R^{12}$—(C=NH)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); and $R^{12}$, wherein $R^{12}$ is alkyl, cycloalkyl, alkenyl, alkynyl, aryl, or aryl alkyl.

"Compounds" as used herein include all stereochemical isomers of said compound.

"Sensitizing activity" or "ability to sensitize" as used herein is intended to include any ability to increase the sensitivity, make sensitive or make susceptible a bacterium to an antibacterial agent.

"Polymyxin ring moiety" or "A" includes the ring portion of polymyxin A, polymyxin B, IL-polymyxin-$B_1$, polymyxin D, polymyxin E, polymyxin F, polymyxin M, polymyxin S, polymyxin T, circulin A, octapeptin A, octapeptin B, octapeptin C, octapeptin D, and derivatives thereof. Examples of derivatives include moieties with modifications which do not substantially effect the ability of the ring moiety to perform its intended function, i.e., as an antibiotic and/or its ability to sensitize bacterium to one or more antibacterial agents. The term "polymyxin B ring moiety" refers to the ring portion of polymyxin B (i.e., cy[Dab-Dab-DPhe-Leu-Dab-Dab-Thr-]). Other examples of polymyxin ring moieties include moieties of the formula:

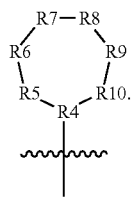

wherein:

R4 is an amino acid residue comprising a functional side chain able to cyclicize the molecule;

R5, R8, and R9 are independently selected cationic or neutral amino acid residues;

R6 is an optionally substituted hydrophobic amino acid residue;

R7 is an optionally substituted hydrophobic residue; and

R10 is Leu or any non-hydrophobic amino acid residues. R4-R10 are discussed in further detail in Formula (V).

The term "prodrug" includes moieties which are cleaved in vivo to yield an active polymyxin derivative compound of the invention. The prodrugs include moieties which mask or otherwise neutralize the positive charges (i.e., the —$NH_3^+$ or other protonated species) at physiological pH. Once the prodrug is administered to the subject, the prodrug moieties or charge masking moieties will be cleaved or other wise removed to yield the active polymyxin derivative of the invention, optionally with three positive charges at physiological pH.

The term "charge masking moiety" includes moieties that reversibly neutralize positive charges on the derivatives. Preferably, the moieties are cleaved or otherwise disassociated with the positive charges of the polymyxin compound after being administered to a subject. Examples of charge masking moieties include sulfoalkyl (e.g., sulfomethylated derivatives). Other positive charge masking moieties include, but are not limited to, chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)).

The term "subject" includes organisms capable of suffering from bacterial infections. Examples of subjects include mammals, e.g., horses, cows, pigs, sheep, goats, cats, dogs, rabbits, ferrets, monkeys, and, preferably, humans.

ABBREVIATIONS

Fatty acids: FA, fatty acyl residue; 6-MOA and MOA, 6-methyloctanoyl residue; 6-MHA and MHA, 6-methylheptanoyl residue; MO(H)A, the mixture of 6-methyloctanoyl, 6-methylheptanoyl and related fatty acyl residues occurring in polymyxin B; OHMDA, 3-OH-8-methyldecanoic acid; OA, octanoyl; DA, decanoyl.

Amino acids: Dab, α,γ-diamino-n-butyryl residue; fDab, N-γ-formyl diamino-n-butyryl residue; acDab, N-γ-acetyl-diamino-n-butyryl residue; Abu, α-aminobutyryl residue; Asn, aspartyl residue; Thr, threonyl residue; Ser, serinyl residue; Phe, phenylalanyl residue; Leu, leucyl residue; Ile, iso-leucyl residue; Ala, alanyl residue; sm-Dab, γ-sulphomethylated α,γ-diamino-n-butyryl residue.

One-letter codes for modified amino acyl residues: X, Dab; Z, Abu; B, N-γ-fDab; J, N-γ-acDab.

Peptides: DAPB, deacylpolymyxin B; DAC, deacylcolistin; PMBN, polymyxin B nonapeptide; PMEN, polymyxin E nonapeptide; PMBO, polymyxin B octapeptide; PMHP, polymyxin B heptapeptide.

Other: cy, cyclo (to denote the cyclic part of the peptide, enclosed within brackets); f, formyl; ac, acetyl; sm, sulfomethyl; MS, methanesulfonate; LPS, lipopolysaccharide; OM, outer membrane; MIC, minimum inhibitory concentration; CFU, colony forming unit. The symbol * is used herein to mark the residues between which the heptapeptide ring portion of the compound is closed leaving the remaining part of the molecule as a side chain.

DETAILED DESCRIPTION OF THE INVENTION

It has now been found that polymyxin derivatives containing at least two (2) but no more than three (3) positive charges still possess antibacterial activity against Gram-negative bacteria, and/or possess the ability to sensitize Gram-negative bacteria to antibacterial agents, such as antibiotics, semisynthetic antibiotics, chemotherapeutic agents and host defence factors, such as complement.

This reduction of positive charges may improve the pharmacological properties of the derivatives according to the present invention when compared to natural polymyxins and their known derivatives. More specifically, it may reduce the toxicity, including nephrotoxicity, of the compounds, and/or reduce the histamine liberation from the host tissue, exerted by the compounds, and/or result in more suitable pharmacokinetic properties such as longer serum half life, increased renal clearance, increased urinary recovery, and/or lower susceptibility to the inactivation by polyanionic tissue and pus constituents, as compared to clinically used polymyxins and their previously described and characterized derivatives, such as polymyxin B nonapeptide.

The present invention thus relates to a polymyxin derivative which may be represented by the general formula I:

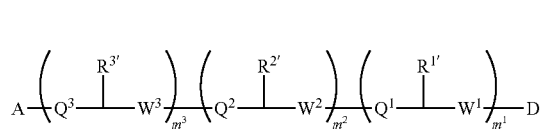

(I)

wherein:

A is a polymyxin ring moiety;

D is a terminal moiety;

$m^1$, $m^2$, and $m^3$ are each independently 0 or 1;

$Q^1$, $Q^2$, and $Q^3$ are each independently $CH_2$, C=O, or C=S;

$W^1$, $W^2$, and $W^3$ are each independently $NR^4$, O, or S;

$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl; and $R^4$ is hydrogen or alkyl, and pharmaceutically acceptable prodrugs and salts thereof, wherein said derivative has at least two but no more than three positive charges at physiological pH, provided that when (1) A is a polymyxin B ring moiety, and $m^1$, $m^2$, and $m^3$ are each 0, then D is not octanoyl; (2) when D is (S)-6-methyloctanoyl, hexanoyl, myristoyl, octanoyl or octanoyl-Dab, then $R^3$ is not the side chain of Dab; or (3) provided that said derivative is not 8,9-diformylated polymyxin B.

Examples of prodrugs of these derivatives include those with charge masking moieties which neutralize the positive charges when administered to the subject which are removed in vivo to yield the compound with three positive charges. Examples of charge masking moieties include sulfoalkyl moieties such as sulfomethyl.

Preferably, the derivatives have three positive charges at physiological pH, as defined above. In certain embodiments of the invention, $R^{1'}$, $R^{2'}$, and $R^{3'}$ do not comprise positively charged functional groups at physiological pH. $R^{1'}$, $R^{2'}$, and $R^{3'}$ may comprise, for example, one or two or more carbamyl, hydroxyl, carboxylate, thiol, sulfate, sulfonyl, or phosphate groups. However, in certain embodiments of the invention, $R^{1'}$, $R^{2'}$ and $R^{3'}$ may comprise one or more positively charged functional groups.

In one embodiment, $m^1$ is 0 and $m^2$ and $m^3$ are each 1. In another, $Q^2$ and $Q^3$ are each C=O and $W^2$ and $W^3$ are each NH.

In certain embodiments, $R^{2'}$ is substituted with one or more groups selected from carbamyl, hydroxyl, carboxylate, thiol, sulfate, sulfonyl, or phosphate groups. Preferably, $R^{2'}$ is substituted with a carbamyl, hydroxyl or carboxylate group. Examples of $R^{2'}$ include alanine, aminobutyric acid, asparagine, aspartic acid, diaminobutyric acid, glutamic acid, glutamine, serine, and threonine, in either L or D configuration. Preferably, $R^{2'}$ is the side chain of D-alanine, L-serine, or L-threonine.

In certain embodiments, $R^{3'}$ is substituted with one or more groups selected from carbamyl, hydroxyl, carboxylate, thiol, sulfate, sulfonyl, or phosphate. Preferably, $R^{3'}$ is substituted alkyl and maybe substituted with a carbamyl, hydroxyl or carboxylate group. Examples of $R^{3'}$ include alanine, aminobutyric acid, asparagine, aspartic acid, diaminobutyric acid, glutamic acid, glutamine, serine, and threonine, in either L or D configuration. Preferably, $R^{3'}$ is D-alanine, L-aminobutyric acid, L-asparagine, D-asparagine, L-diaminobutyric acid, L-serine, D-serine, or D-threonine.

Examples of A include the ring moiety of polymyxin B (i.e., cy[Dab-Dab-DPhe-Leu-Dab-Dab-Thr-]) and polymyxin E (i.e., cy[Dab-Dab-DLeu-Leu-Dab-Dab-Thr-].

In a further embodiment, the terminal moiety is selected from the group consisting of a hydrophobic oligopeptide, $R^{12}$—(C=O); $R^{12}$—$SO_2$—; $R^{12}$—(C=NH)—; $R^{12}$—NH—(C=O)—; $R^{12}$—NH—(C=S)—; $R^{12}$—NH—(C=O)—; $R^{12}$—NH—(C=NH)—; $R^{12}$—O—(C=S)—; $R^{12}$—O—(C=O); $R^{12}$—P(O)OH—; $R^{12}$—(C=S); or $R^{12}$, wherein $R^{12}$ is alkyl, cycloalkyl, alkenyl, alkynyl, aryl, or aryl alkyl. In certain embodiments, D is $R^{12}$—(C=O) or $R^{12}$—(C=S).

Examples of hydrophobic oligopeptides that can be used in the derivatives of the invention include oligopeptides of 1-10, or, preferably, 2-5, amino acyl residues (e.g., Leu, Ile, Phe, or Trp), such as, but not limited to Leu-Leu-Leu, Ile-Leu-Ile, Phe-Ile-Leu and Trp-Trp-Ile.

Examples of D include octanoyl, nonanoyl, isononanoyl, decanoyl, isodecanoyl, undecanoyl, dodecanoyl, tetradecanoyl, cyclohexyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl, heptanoyl, and 9-fluorenylmethoxycarbonyl. In a further embodiment, D contains 6 to 18 carbon atoms. In a further embodiment, D is 6-methyloctanoyl; 6-methylheptanoyl; 3-OH-8-methyldecanoyl; or octanoyl.

In a further embodiment, A is a polymyxin ring moiety selected from that of polymyxin A, polymyxin B, IL-polymyxin-$B_1$, polymyxin D, polymyxin E, polymyxin F, polymyxin M, polymyxin S, polymyxin T, circulin A, octapeptin A, octapeptin B, octapeptin C, octapeptin D, or derivatives thereof. Preferably, A is a polymyxin ring moiety of polymyxin B or polymyxin E.

In another embodiment, the invention pertains to polymyxin derivatives of formula (II):

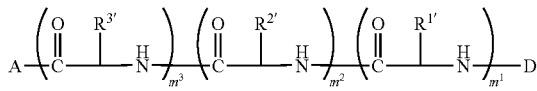

(II)

wherein:
A is a polymyxin ring moiety;
D is a hydrophobic oligopeptide, $R^{12}$—C(=O) or $R^{12}$—C(=S);
$m^1$, $m^2$, and $m^3$ are each independently 0 or 1;
$R^{1'}$, $R^{2'}$, and $R^{3'}$ are each independently side chains of natural or unnatural amino acids, alkyl, alkenyl, alkyl, arylalkyl, aryl, alkoxy, alkoxycarbonyl, aryloxycarbonyl, alkylamino, or alkynyl; and
$R^{12}$ is $C_5$-$C_{17}$ alkyl, $C_5$-$C_{17}$ alkenyl, $C_5$-$C_{17}$ aryl, $C_5$-$C_{17}$ arylalkyl or $C_5$-$C_{17}$ alkynyl, and pharmaceutically acceptable prodrugs and salts thereof, wherein said derivative has at least two and no more than three positive charges at physiological pH, and provided (1) when A is a polymyxin B ring moiety, and $m^1$, $m^2$, and $m^3$ are each 0, then D is not octanoyl; (2) when D is (S)-6-methyloctanoyl, hexanoyl, myristoyl, octanoyl or octanoyl-Dab, then $R^3$ is not the side chain of Dab; or (3) provided that said derivative is not 8,9-diformylated polymyxin B.

Preferably, the derivative of formula (II) has three positive charges at physiological pH. In a further embodiment, $m^1$ may be 0 and/or $m^2$ and $m^3$ may each be 1. In a further embodiment, $R^{2'}$ and/or $R^{3'}$ may each independently be substituted alkyl (e.g., substituted with a carbamyl, hydroxyl or carboxylate group). Furthermore, $R^{2'}$ and/or $R^{3'}$ may each be the side chain of alanine, aminobutyric acid, asparagine, aspartic acid, diaminobutyric acid, glutamic acid, glutamine, serine, and threonine, in either the L or D configuration. Preferably, $R^{2'}$ is the side chain of D-alanine, L-serine, or L-threonine and $R^{3'}$ is D-alanine, L-aminobutyric acid, L-asparagine, D-asparagine, L-diaminobutyric acid, L-serine, D-serine, or D-threonine.

In a further embodiment, $R^{12}$ is alkyl. Examples of D include octanoyl, nonanoyl, isononanoyl, decanoyl, isodecanoyl, undecanoyl, dodecanoyl, tetradecanoyl, cyclohexyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl, heptanoyl, and 9-fluorenylmethoxycarbonyl.

In another embodiment, the invention pertains to polymyxin derivatives of formula (III):

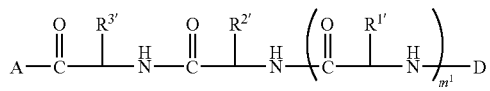

(III)

wherein:
A is a polymyxin B or polymyxin E ring moiety;
D is $R^{12}$—C(=O) or $R^{12}$—C(=S);
$m^1$ is 0 or 1;
$R^{1'}$, $R^{2'}$, and $R^{3'}$ are each independently side chains of natural or unnatural amino acids, alkyl, alkenyl, arylalkyl, aryl, alkoxy, alkoxycarbonyl, aryloxycarbonyl, alkylamino, or alkynyl, wherein at least one of $R^{2'}$ and $R^{3'}$ comprise a carbamyl, hydroxyl or carboxylate group; and $R^{12}$ is $C_5$-$C_{17}$ alkyl, and pharmaceutically acceptable prodrugs and salts thereof, wherein said derivative has at least two but no more than three positive charges at physiological pH, and provided (1) when D is (S)-6-methyloctanoyl, hexanoyl, myristoyl, octanoyl or octanoyl-Dab, then $R^3$ is not the side chain of Dab; or (2) said derivative is not 8,9-diformylated polymyxin B.

Preferably, the compounds of the invention have three positive charges at physiological pH, $m^1$ is 0, $R^{2'}$ and $R^{3'}$ are both substituted alkyl, and/or D is octanoyl, nonanoyl, isononanoyl, decanoyl, isodecanoyl, undecanoyl, dodecanoyl, tetradecanoyl, cyclohexyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl or heptanoyl.

In another embodiment, the invention also pertains to polymyxin derivatives of formula (IV):

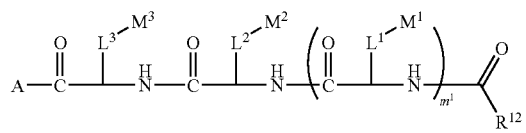

(IV)

wherein:

A is a polymyxin B or polymyxin E ring moiety;

$m^1$ is 0 or 1;

$L^1$, $L^2$ and $L^3$ are each independently $C_1$-$C_3$ alkyl or a covalent bond;

$M^1$, $M^2$ and $M^3$ are each independently H, $NH_2$, C(=O)$NH_2$, C(=O)OH, or —OH;

$R^{12}$ is $C_5$-$C_{17}$ alkyl, and pharmaceutically acceptable prodrugs and salts thereof, and wherein said derivative has at least two but no more than three positive charges at physiological pH, and provided (1) when D is (S)-6-methyloctanoyl, hexanoyl, myristoyl, octanoyl or octanoyl-Dab, then $R^3$ is not the side chain of Dab; or (2) said derivative is not 8,9-diformylated polymyxin B.

Examples of $L^2$ include branched alkyl (e.g., —CH($CH_3$)—) and methylene (—$CH_2$). Examples of $M^2$ include OH and H. In another embodiment, $L^3$ is —$CH_2$— and $M^3$ is OH or H. In yet another embodiment, $L^3$ is —$CH_2$—$CH_2$— and $M^3$ is C(=O)$NH_2$. Other examples of $L^3$ include —CH($CH_3$)— and CH($CH_2CH_3$)— wherein $M^3$ is OH or $NH_2$ In yet another embodiment, the invention also pertains to polymyxin derivatives of the general formula (V),

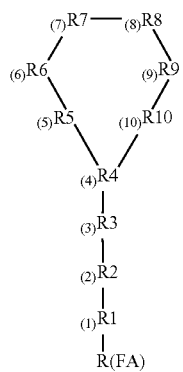

(V)

wherein R4 is an amino acid residue comprising a functional side chain able to cyclicize the molecule;

R6 is an optionally substituted hydrophobic amino acid residue;

R7 is an optionally substituted hydrophobic residue;

R10 is Leu or any non-hydrophobic amino acid residue; and wherein R1, R2, and R3 are optional; and wherein R1, R2, R3, R5, R8 and R9 are amino acid residues selected so that the total number of positive charges at physiological pH is at least two and no more than three; and wherein R(FA) is an optionally substituted alkanoyl or alkyl residue or a hydrophobic oligopeptide;

or a pharmaceutically acceptable prodrug or salt thereof, provided that (1) when R8 and R9 are formylated, R(FA)-R1-R2-R3 does not constitute a native polymyxin B side chain; (2) when R4-R10 is a polymyxin B ring moiety and R1, R2, and R3 are each absent, then R(FA) is not octanoyl, or (3) when R(FA) is (S)-6-methyloctanoyl, hexanoyl, myristoyl, octanoyl or octanoyl-Dab, then $R^3$ is not the side chain of Dab.

In natural polymyxins and octapeptins, R(FA) is 6-methyloctanoic acid (6-MOA), 6-methylheptanoic acid (6-MHA), octanoic acid, heptanoic acid, nonanoic acid, 3-OH-6-methyloctanoic acid, 3-OH-8-methyldecanoic acid, 3-OH-8-methylnonanoic acid, 3-OH-8-decanoic acid, and 3-OH-6-methyloctanoic acid. Examples of known derivatives that have antibacterial activity include those wherein R(FA) is γ-phenylbutyric acid, isovaleric acid, 9-fluorenyl-methoxycarbonic acid, a series of C:9 to C:14 unbranched fatty acids as well as iso C:9 and iso C:10 fatty acids.

In a derivative according to the present invention, R(FA) may be any hydrophobic fatty acid residue, or may be selected from the group consisting of octanoyl, decanoyl and 6-MHA residues.

A person skilled in the art may readily recognize equivalents of these preferred hydrophobic R(FA) residues, which may be selected from the group consisting of e.g. optionally substituted acyl or alkyl residue, an optionally substituted isoalkyl residue, an optionally substituted cycloalkyl residue, an optionally substituted alkenyl residue, an optionally substituted cycloalkenyl residue, an optionally substituted aryl residue, an optionally substituted heteroaryl residue, an optionally substituted heterocyclic residue, wherein said residues preferably have more than five (5) carbon atoms and wherein the substitutions may also include those optionally designed between the residue and the N-terminus of the peptide. R(FA) may also be a stretch of a hydrophobic oligopeptide. Examples of possible R(FA) residues include (but are not limited to) octanoyl, nonanoyl, isononanoyl, decanoyl, isodecanoyl, undecanoyl, dodecanoyl, tetradecanoyl, cyclohexanoyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl, heptanoyl, and 9-fluorenylmethoxycarbonyl residues.

In natural polymyxins and octapeptins, R1 is Dab or absent (i.e., replaced by a covalent bond). Examples of known derivatives that have antibacterial activity include those wherein R1 is Ala or a covalent bond.

In a derivative according to the present invention R1, if present, may be any amino acid residue, provided that the total number of positive charges in said derivative does not exceed three and that the total number of positive charges in the side chain portion does not exceed two, and is preferably Abu, if present.

In natural polymyxins and octapeptins, R2 is Thr or absent (i.e., replaced by a covalent bond). Examples of known derivatives that have antibacterial activity include those wherein R2 is O-acetyl-Thr, O-propionyl-Thr, O-butyryl-Thr or a covalent bond.

In a derivative according to the present invention, R2, if present, may be any amino acid residue, provided that the total number of positive charges in said derivative does not exceed three and that the total number of positive charges in the side chain portion does not exceed two, and is preferably selected from the group consisting of alanine, aminobutyric acid, asparagine, aspartic acid, diaminobutyric acid, glutamic acid, glutamine, serine, and threonine, in either L or D configuration, if present. A person skilled in the art may also recognize an equivalent residue of Thr to be Ser.

In natural polymyxins and octapeptins, R3 is Dab, DDab or DSer. Examples of numerous known synthetic derivatives that have antibacterial activity include those wherein R3 is Lys or 2-amino-4-guanidino butyric acid.

In a derivative according to the present invention, R3, if present, may be any amino acid residue, provided that the total number of positive charges in said derivative does not exceed three and that the total number of positive charges in the chain portion does not exceed two, and is preferably selected from the group consisting of alanine, aminobutyric acid, asparagine, aspartic acid, diaminobutyric acid, glutamic acid, glutamine, serine, and threonine, in either L or D configuration, if present.

A person skilled in the art may readily recognize residues other than these preferred residues R1, R2 and R3, and may select such from a group consisting of e.g. a covalent bond, alanine, 2-aminoadipic acid, α-n-butyric acid, N-(4-aminobutyl)glycine, α-aminobutyric acid, γ-aminobutyric acid, α-amino-caproic acid, aminocyclopropanecarboxylate, aminoisobutyric acid, aminonorbornylcarboxylate, α-amino-n-valeric acid, arginine, $N_\omega$-methyl arginine, asparagine, α-methylaspartate, aspartic acid, N-benzylglycine, N-(2-carbamylethyl)glycine, N-(carbamylethyl)glycine, 1-carboxy-1(2,2-diphenyl ethylamino)cyclopropane, cysteine, $N_\alpha$-methyldiamino-n-butyric acid, $N_\gamma$-acetyldiamino-n-butyric acid, $N_\gamma$-formyldiamino-n-butyric acid, $N_\gamma$-methyldiamino-n-butyric acid, N-(N-2,2-diphenylethyl)carbamylmethyl-glycine, N-(N-3,3-diphenylpropyl)carbamylmethyl(1)glycine, N-(3,3-diphenylpropyl) glycine, glutamic acid, glutamine, glycine, t-butylglycine, 2-amino-4-guanidinobutyric acid, N-(3-guanidinopropyl)glycine, histidine, homophenylalanine, isodesmosine, isoleucine, leucine, norleucine, hydroxylysine, $N_\alpha$-methyllysine, lysine, $N_\alpha$-methylhydroxylysine, N-methyllysine, $N_\epsilon$-acetylhydroxylysine, $N_\epsilon$-acetyl lysine, $N_\epsilon$-formylhydroxylysine, $N_\epsilon$-formyllysine, $N_\epsilon$-methylhydroxylysine, $N_\epsilon$-methyllysine, methionine, α-methyl-γ-aminobutyrate, α-methyl-aminoisobutyrate, α-methylcyclohexylalanine, α-napthylalanine, norleucine, norvaline, α-methylornithine, $N_\alpha$-methylornithine, $N_\delta$-acetylornithine, $N_\delta$-formyl-ornithine, $N_\delta$-methylornithine, ornithine, penicilamine, phenylalanine, hydroxyproline, proline, $N_\alpha$-methyldiamino-n-propionic acid, $N_\beta$-acetyldiamino-n-propionic acid, $N_\beta$-formyldiamino-n-propionic acid, $N_\beta$-methyldiamino-n-propionic acid, phosphoserine, serine, phosphothreonine, threonine, tryptophan, tyrosine, norvaline, and valine.

In natural polymyxins and octapeptins, R4 is Dab. Examples of synthetic derivatives that have antibacterial activity include those wherein R4 is Lys.

In a derivative according to the present invention R4 is an amino acid residue comprising a functional side chain able to cyclicize the molecule, and may be selected from the group of equivalent residues consisting of Lys, hydroxylysine, ornithine, Glu, Asp, Dab, diaminopropionic acid, Thr, Ser and Cys, preferably Dab.

In natural polymyxins and octapeptins, R5, R8 and R9 are Dab. Examples of synthetic derivatives that have antibacterial activity include those wherein R5, R8, and R9 may be Lys or 2-amino-4-guanidino butyric acid.

In a derivative according to the present invention R5, R8 and R9 may be a positively charged or a neutral amino acid residue, preferably Dab or Abu, provided that the total number of positive charges in said derivative does not exceed three.

A person skilled in the art, may readily recognize equivalent residues of these preferred residues, and may select such from a group consisting of e.g. diaminobutyric acid, diaminopropionic acid, lysine, hydroxylysine, ornithine, 2-amino-4-guanidinobutyric acid, glycine, alanine, valine, leucine, isoleucine, phenylalanine, D-phenylalanine, methionine, threonine, serine, α-amino-n-butyric acid, α-amino-n-valeric acid, α-amino-caproic acid, $N_\epsilon$-formyl-lysine, $N_\epsilon$-acetyllysine, $N_\epsilon$-methyllysine, $N_\epsilon$-formylhydroxylysine, $N_\epsilon$-acetylhydroxylysine, $N_\epsilon$-methylhydroxylysine, L-$N_\alpha$-methylhydroxylysine, $N_\gamma$-formyldiamino-n-butyric acid, $N_\gamma$-acetyldiamino-n-butyric acid, $N_\gamma$-methyldiamino-n-butyric acid, $N_\beta$-formyldiamino-n-propionic acid, D-$N_\beta$-formyldiamino-n-propionic acid, $N_\beta$-acetyldiamino-n-propionic acid, $N_\beta$-methyldiamino-n-propionic acid, $N_\delta$-formylornithine, $N_\delta$-acetylornithine and $N_\delta$-methylornithine.

In natural polymyxins and octapeptins, R6 is DPhe or DLeu and R7 is Leu, Ile, Phe or Thr. Synthetic derivatives that have antibacterial activity include those wherein R6 is DTrp and wherein R7 is Ala.

In a derivative according to the present invention, R6 is an optionally substituted hydrophobic amino acid residue, preferably DPhe or DLeu, and R7 is an optionally substituted hydrophobic residue, preferably Leu, Thr or Ile.

A person skilled in the art may readily recognize equivalent residues of these preferred hydrophobic residues, and may select such from a group consisting of e.g. phenylalanine, α-amino-n-butyric acid, tryptophane, leucine, methionine, valine, norvaline, norleucine, isoleucine and tyrosine. A person skilled in the art may also recognize the equivalent residue of threonine to be serine.

In natural polymyxins and octapeptins, R10 is Thr and Leu. Examples of known derivatives that have antibacterial activity include those wherein R10 is O-acetyl-Thr, O-propionyl-Thr or O-butyryl-Thr.

In a derivative according to the present invention, R10 is Leu or any non-hydrophobic amino acid residue, provided that that the total number of positive charges in said derivative does not exceed three. Preferably R10 is Thr or Leu.

A person skilled in the art may also recognize the equivalent residue of threonine to be serine.

More specifically, preferred residues are chosen in such a manner that R8 and R9 are not both formylated when R(FA)-R1-R2-R3 constitutes the native polymyxin B sidechain; and R4 is not directly linked to octanoyl residue when R4-R10 constitutes a native polymyxin B ring structure.

The specific positions of the at the most three (3) positive charges referred to herein above can be located in the heptapeptide ring portion and/or in the side chain, if present. When three (3) positive charges are present in the derivatives according to the invention, said three (3) positive charges can be located in the heptapeptide ring portion; or two (2) positive charges can be located in heptapeptide ring portion while the remaining one positive charge is located in the side chain; or one (1) positive charge can be located in the heptapeptide ring portion while the remaining two (2) positive charges are located in the side chain. Preferably at least two (2) positive charges are located in the heptapeptide ring portion.

In one embodiment, derivatives according to the present invention can be selected from the group of derivatives wherein R1-R10 is selected from the group consisting of Thr-DSer-cy[Dab-Dab-DPhe-Leu-Dab-Dab-Thr-]; Thr-DThr-cy[Dab-Dab-DPhe-Thr-Dab-Dab-Thr-]; Thr-DSer-cy[Dab-Dab-DPhe-Thr-Dab-Dab-Thr-]; Thr-Abu-cy[Dab-Dab-DPhe-Leu-Dab-Dab-Thr-]; Abu-Thr-Abu-cy[Dab-Dab-DPhe-Leu-Dab-Dab-Thr-]; Thr-Dab-cy[Dab-Dab-DPhe-Leu-Abu-Dab-Thr-]; Thr-Abu-cy[Dab-Dab-DPhe-Leu-Dab-Dab-Leu-]; Thr-DAla-cy[Dab-Dab-DPhe-Thr-Dab-Dab-Thr-]; Thr-Dab-cy[Dab-Dab-DPhe-Leu-Dab-Abu-Thr-]; Thr-Abu-cy[Dab-Dab-DLeu-Leu-Dab-Dab-Thr-]; DAla-DAla-cy[Dab-Dab-DPhe-Leu-Dab-Dab-Thr-]; cy[Dab-Dab-DPhe-Leu-Dab-Dab-Thr-], Abu-cy[Dab-Dab-DPhe-Leu-Dab-Dab-Thr-]; Thr-Dab-cy[Dab-Abu-DPhe-Leu-Dab-Dab-Thr-]; Dab-Thr-Dab-cy[Dab-Dab-DPhe-Leu-Abu-Abu-Thr-]; Thr-Abu-cy[Dab-Lys-DPhe-Leu-Dab-Dab-Thr-]; Thr-Abu-cy[Dab-Abu-DPhe-Leu-Dab-Dab-Thr-]; Thr-Abu-cy[Dab-Dab-DPhe-Leu-Dab-Abu-Thr-]; Thr-Ser-cy[Dab-Dab-DPhe-Leu-Dab-Dab-Thr-]; Thr-Asn-cy[Dab-Dab-DPhe-Leu-Dab-Dab-Thr-]; Thr-Thr-DSer-cy[Dab-Dab-DPhe-Leu-Dab-Dab-Thr-]; and Ala-Thr-DSer-cy[Dab-Dab-DPhe-Leu-Dab-Dab-Thr-].

In other embodiments, derivatives according to the present invention can be selected from the group consisting of: OA-Thr-DSer-cy[Dab-Dab-DPhe-Leu-Dab-Dab-Thr-]; DA-Thr-DSer-cy[Dab-Dab-DPhe-Leu-Dab-Dab-Thr-]; OA-Thr-DThr-cy[Dab-Dab-DPhe-Thr-Dab-Dab-Thr-]; OA-Thr-DSer-cy[Dab-Dab-DPhe-Thr-Dab-Dab-Thr-]; DA-Thr-Abu-cy[Dab-Dab-DPhe-Leu-Dab-Dab-Thr-]; OA-Thr-Abu-cy[Dab-Dab-DPhe-Leu-Dab-Dab-Thr-]; MHA-Thr-Abu-cy[Dab-Dab-DPhe-Leu-Dab-Dab-Thr-]; MHA-Abu-Thr-Abu-cy[Dab-Dab-DPhe-Leu-Dab-Dab-Thr-]; OA-Thr-Dab-cy[Dab-Dab-DPhe-Leu-Abu-Dab-Thr-]; OA-Thr-Abu-cy[Dab-Dab-DPhe-Leu-Dab-Dab-Leu-]; OA-Thr-DAla-cy[Dab-Dab-DPhe-Thr-Dab-Dab-Thr-]; OA-Thr-Dab-cy[Dab-Dab-DPhe-Leu-Dab-Abu-Thr-]; OA-Thr-Abu-cy[Dab-Dab-DLeu-Leu-Dab-Dab-Thr-]; OA-DAla-DAla-cy[Dab-Dab-DPhe-Leu-Dab-Dab-Thr-]; DA-cy[Dab-Dab-DPhe-Leu-Dab-Dab-Thr-]; OA-Abu-cy[Dab-Dab-DPhe-Leu-Dab-Dab-Thr-]; OA-Thr-Dab-cy[Dab-Abu-DPhe-Leu-Dab-Dab-Thr-]; MHA-Dab-Thr-Dab-cy[Dab-Dab-DPhe-Leu-Abu-Abu-Thr-]; OA-Thr-Abu-cy[Dab-Lys-DPhe-Leu-Dab-Dab-Thr-]; OA-Thr-Abu-cy[Dab-Abu-DPhe-Leu-Dab-Dab-Thr-]; OA-Thr-Abu-cy[Dab-Dab-DPhe-Leu-Dab-Abu-Thr-]; OA-Thr-Ser-cy[Dab-Dab-DPhe-Leu-Dab-Dab-Thr-]; OA-Thr-Asn-cy[Dab-Dab-DPhe-Leu-Dab-Dab-Thr-]; OA-Thr-Thr-DSer-cy[Dab-Dab-DPhe-Leu-Dab-Dab-Thr-]; and OA-Ala-Thr-DSer-cy[Dab-Dab-DPhe-Leu-Dab-Dab-Thr-].

Preferably, derivatives according to the present invention are selected from the group consisting of: OA-Thr-DSer-cy[Dab-Dab-DPhe-Leu-Dab-Dab-Thr-]; DA-Thr-DSer-cy[Dab-Dab-DPhe-Leu-Dab-Dab-Thr-]; OA-Thr-DThr-cy[Dab-Dab-DPhe-Thr-Dab-Dab-Thr-]; OA-Thr-DSer-cy[Dab-Dab-DPhe-Thr-Dab-Dab-Thr-]; DA-Thr-Abu-cy[Dab-Dab-DPhe-Leu-Dab-Dab-Thr-]; OA-Thr-Abu-cy[Dab-Dab-DPhe-Leu-Dab-Dab-Thr-]; MHA-Thr-Abu-cy[Dab-Dab-DPhe-Leu-Dab-Dab-Thr-]; MHA-Abu-Thr-Abu-cy[Dab-Dab-DPhe-Leu-Dab-Dab-Thr-]; OA-Thr-Dab-cy[Dab-Dab-DPhe-Leu-Abu-Dab-Thr-]; OA-Thr-Abu-cy[Dab-Dab-DPhe-Leu-Dab-Dab-Leu-]; OA-Thr-DAla-cy[Dab-Dab-DPhe-Thr-Dab-Dab-Thr-]; OA-Thr-Dab-cy[Dab-Dab-DPhe-Leu-Dab-Abu-Thr-]; OA-Thr-Abu-cy[Dab-Dab-DLeu-Leu-Dab-Dab-Thr-]; OA-DAla-DAla-cy[Dab-Dab-DPhe-Leu-Dab-Dab-Thr-]; DA-cy[Dab-Dab-DPhe-Leu-Dab-Dab-Thr-]; OA-Thr-Ser-cy[Dab-Dab-DPhe-Leu-Dab-Dab-Thr-]; OA-Thr-Asn-cy[Dab-Dab-DPhe-Leu-Dab-Dab-Thr-]; OA-Thr-Thr-DSer-cy[Dab-Dab-DPhe-Leu-Dab-Dab-Thr-]; and OA-Ala-Thr-DSer-cy[Dab-Dab-DPhe-Leu-Dab-Dab-Thr-].

As shown in the example section herein, the compounds according to the present invention carrying only three (3) positive charges can be very potent agents to inhibit the growth of Gram-negative bacteria or to sensitize them to antibacterial agents, and even derivatives carrying only two (2) positive charges can have the same effect, although at a more moderate level.

For direct antibacterial activity at least two (2) and more preferably three (3) positive charges are located in the heptapeptide ring portion, and for sensitizing activity at least one (1) and more preferably two (2) or three (3) positive charges are located in the heptapeptide ring part. Furthermore, the presence of two hydroxyl groups in the side chain part significantly enhances the direct antibacterial activity.

The works of Teuber (1970), Srinivasa and Ramachandran (1980a), and Sakura et al. (2004) disclose, among other polymyxin derivatives, derivatives having only two (2) or three (3) positive charges. However, the antibacterial activity of the disclosed derivatives is very weak and clinically irrelevant (Sakura et al. 1980), attributed to amino acid residues in full contradiction to the findings of the present invention (Srinivasa and Ramachandran 1980a) or attributed to no specific amino acid residues at all, due to incomplete purification (Teuber 1970). Furthermore, none of the works cited above describe, suggest or motivate to study the ability of such derivatives to sensitize Gram-negative bacteria to antibacterial agents. As the examples of the present invention clearly show, one cannot predict the ability of a polymyxin derivative to sensitize Gram-negative bacteria to antibacterial agents on the basis of its ability to inhibit the growth of the same. For example, whereas a clinically irrelevant concentration of octanoyl polymyxin B heptapeptide of as high as 128 µg/ml is needed to inhibit the growth of E. coli (Sakura et al. 2004), an amount as low as 4 µg is enough for a moderate sensitization of the bacterium to rifampin, as shown in the example section herein.

The acetylated polymyxin derivatives described by Teuber (1970) are mixtures of differently acetylated derivatives. Acetic anhydride can react with any of the five free amino groups of the polymyxin B molecule to yield a monoacetylated polymyxin. Therefore a monoacetylated polymyxin according to Teuber is a mixture of five monoacetylated polymyxin derivatives, each acetylated at a different amino group. A diacetylated polymyxin according to Teuber is a mixture of ten differently diacetylated derivatives and triacetylated polymyxin is also a mixture of ten differently triacetylated derivatives. Teuber did not attempt to isolate these derivatives from the mixtures. The problem with such modified polymyxins is that the partial modification may result in reduced specificity. Therefore, some of the amino groups that are important for the antibacterial activity are partially substituted (and hence inactivated) whereas some of the non-important amino groups remain partially unsubstituted. Furthermore, the degree of substitution may lead to lot-to-lot variations.

The polymyxin derivatives according to the present invention, on the other hand, are isolated and structurally clearly defined and identified compounds.

Srinivasa and Ramachandran (1980a) proposed that the free side chain amino groups of triformyl-polymyxin B in residues R1 and R3, as well as the free amino groups of diformylpolymyxin B in residues R1, R3, and R5 are essential while the free amino groups in R8 and R9 are not essential for the growth inhibition of Pseudomonas aeruginosa. As a contrast to their conclusions, the compounds in the present invention include those that lack the free amino groups in R1 and R3, carry them in R5, R8 and R9, and yet are potent agents against *Ps. aeruginosa* as well as other Gram-negative bacteria.

A shortened polymyxin B derivative octanoyl polymyxin B heptapeptide has been disclosed by Sakura et al. (2004). The attachment of the octanoyl residue to the N-terminus of the residue R4 of the polymyxin B heptapeptide results in a compound having only three (3) positive charges. Sakura et al. found that octanoyl polymyxin B heptapeptide inhibits the growth of bacteria only at a very high (and clinically irrelevant) concentration (128 µg/ml), whereas the other derivatives such as octanoyl polymyxin B octapeptide and octanoyl polymyxin B nonapeptide, both having four charges (4) are very potent agents to inhibit bacterial growth. Sakura et al. did not disclose or suggest the ability of octanoyl polymyxin B heptapeptide to sensitize bacteria to antibacterial agents, nor teach that a longer fatty acid tail increases its antibacterial activity, as shown in the example section herein.

The present invention in one aspect provides new polymyxin derivatives having two (2) or three (3) positive charges only and still being capable of inhibiting the growth of one or more Gram-negative bacterial species and or sensitizing one or more Gram-negative bacterial species to an antibiotic or antibacterial agent.

The susceptibility of bacteria to an antibacterial agent may be determined by two microbiological methods. A rapid but crude procedure uses commercially available filter paper disks that have been impregnated with a specific quantity of the antibacterial agent. These disks are placed on the surface of agar plates that have been inoculated with a suspension of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration (MIC).

Derivatives according to the present invention may inhibit the growth of or sensitize to antibacterial agents clinically important Gram-negative bacteria such as those belonging to the genus of *Acinetobacter, Aeromonas, Alcaligenes, Bordetella, Branhamella, Campylobacter, Citrobacter, Enterobacter, Escherichia, Francisella, Fusobacterium, Haemophilus, Helicobacter, Klebsiella, Legionella, Moraxella, Pasteurella, Plesiomonas, Pseudomonas, Salmonella, Serratia, Shigella*, and *Yersinia* species. The bacteria may be, for example, *Escherichia coli, Klebsiella pneumoniae, Klebsiella oxytoca, Enterobacter cloacae, Enterobacter aerogenes*, other species of *Enterobacter, Citrobacter freundii, Pseudomonas aeruginosa*, other species of *Pseudomonas, Acinetobacter baumannii*, as well as many other species of non-fermentative Gram-negative bacteria. The bacteria also include *Helicobacter pylori*, as well as other clinically important Gram-negative bacteria.

The bacterial infections to be treated include, for example, bacteremia, septicemia, skin and soft tissue infection, pneumonia, meningitis, infections in the pelveoperitoneal region, foreing body infection, fever in hematological patient, infection associated with an intravenous line or other catheter, canyl and/or device, infection in gastrointestinal tract, in the eye, or in the ear, superficial skin infection, and colonization of gastrointestinal tract, mucous membranes and/or skin by potentially noxious bacteria.

The bacterial infectious diseases include (but are not limited to) severe hospital-acquired infections, infections of the immunocompromised patients, infections of the organ transplant patients, infections at the intensive care units (ICU), severe infections of burn wounds, severe community-acquired infections, infections of cystic fibrosis patients, as well as infections caused by multi-resistant Gram-negative bacteria.

The present invention is also directed to combinations of two or more derivatives according to the present invention for combination treatment. The combinations may include derivatives having different spectra of antibacterial activity or a capability to sensitize different species or strains of Gram-negative bacteria to antibacterial agents.

Another aspect of the present invention is directed to pharmaceutical compositions comprising polymyxin derivatives according to the present invention, their salt forms, selected combinations thereof, and optionally an antibacterial agent formulated together with one or more pharmaceutically acceptable carriers and excipients. They facilitate processing of the active compounds into preparations which can be used pharmaceutically and include e.g. diluting, filling, buffering, thickening, wetting, dispersing, solubilizing, suspending, emulsifying, binding, stabilizing, disintegrating, encapsulating, coating, embedding, lubricating, colouring, and flavouring agents as well as absorbents, absorption enhancers, humefactants, preservatives and the like, well-known to a person skilled in the art.

Pharmaceutical compositions include compositions wherein the active ingredients are contained in an amount effective to achieve the intended purpose. More specifically, a therapeutically effective amount means an amount of compound effective to treat, prevent, alleviate or ameliorate symptoms of pathology or prolong the survival of the subject being treated at a reasonable benefit to risk ratio applicable to any medical treatment. Determination of a therapeutically effective amount is well within the capability of those skilled in the art of medicine.

Compositions may be produced by processes well known in the art, e.g. by means of conventional mixing, dissolving, encapsulating, entrapping, lyophilizing, emulsifying and granulating processes. The proper formulation is dependent upon the route of administration chosen, and the pharmaceutical composition can be formulated for immediate release or slow release (e.g. in order to prolong the therapeutic effect and/or improve tolerability). Furthermore, the formulations may conveniently be presented in unit dosage form by methods known in the art of pharmacy.

Pharmaceutical compositions according to the present invention include (but are not limited to) those intended for intravenous, intramuscular, oral, or topical administration as well as those being administered as a suppositorium or as an inhalable aerosol. The compositions include intravenous, intramuscular, intraperitoneal, subcutaneous, intramedullary, intrathecal, intraventricular, intranasal, or intraocular injections, inhalable aerosols as well as those intended for rectal, oral, intravaginal, transmucosal or transdermal delivery.

For parenteral administration (e.g. by bolus injection, fast running infusions, or slow infusions), the compounds according to this invention as well as the combinations described above may be formulated as their suitable salt or ester forms in sterile aqueous solutions, preferably physiologically compatible fluids such as saline, 5% dextrose, Ringer's solution, and Hank's solution. The formulation may also include organic solvents such as propylene glycol, polyethylene glycol, propylene glycol or related compounds as well as preservatives and surfactants.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In addition, the pharmaceutical compositions for parental administration may be suspensions or emulsions in oily or aqueous vehicles, and may contain formulatory agents such as suspending, stabilizing and/or dispersing agents. Suitable lipophilic vehicles and solvents include fatty oils such as natural and/or synthetic fatty acids esters, such as ethyl oleate and triglycerides, or liposomes. The suspensions may contain substances, which increase the viscosity of the suspension, such as sodium carboxymethyl cellulose, sorbitol or dextran.

The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use.

For oral administration, solid form preparations include e.g. powders, tablets, pills, dragees, lozenges, capsules, cachets, and microgranular preparations. Pharmaceutical preparations can be made using a solid excipient, optionally grinding the resulting mixture, and processing the mixture of granules, after adding suitable auxiliaries if desired, to obtain tablets or dragee cores. A solid carrier/excipient can be one or more substances which may also act as diluents, solubilizers, lubricants, suspending agents, binders, preservatives, flavouring agents, wetting agents, tablet disintegrating agents, or an encapsulating material. Suitable carriers include, but are not limited to, magnesium carbonate, magnesium stearate, talc, dextrose, lactose, pectin, starch, gelatin, tragacanth, methylcellulose, sodium carboxymethylcellulose, a low melting wax, cocoa butter, and the like.

Liquid preparations suitable for oral administration include, e.g., aqueous solutions, syrups, elixirs, aqueous suspensions, emulsions and gels. Aqueous solutions can be prepared by dissolving the active component in water and adding suitable stabilizing and thickening agents as well as colorants and flavours. Aqueous suspensions can be prepared by dispersing the finely divided active component in water with viscous material, such as natural or synthetic gums, resins, methylcellulose, sodium carboxymethylcellulose, and other well known suspending agents. Emulsions may be prepared in solutions in aqueous propylene glycol solutions or may contain emulsifying agents such as lecithin, sorbitan monooleate or acacia.

The compounds according to the invention or combinations described above may also be formulated for topical administration. The active compounds are admixed under sterile conditions with pharmaceutically acceptable carriers/excipients, including any needed buffering agents and preservatives. Ointments, creams and lotions may, for example, be formulated with an aqueous or oily base with the addition of suitable emulsifying, dispersing, suspending, thickening, stabilizing, or coloring agents. Commonly used excipients include animal and vegetable fats and oils, waxes, paraffins, starch, cellulose derivatives, tragacanth, and polyethylene glycol.

Other topical formulations include, but are not limited to, ear-drops, eye-drops and transdermal patches.

For transdermal as well as transmucosal administration, penetrants generally known in the art may be used in the formulation.

For administration by inhalation, the compounds according to this invention and the combinations described above are delivered in the form of an aerosol spray presentation from a ventilator, pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compounds according to this invention and the combinations described above may also be formulated in rectal compositions such as retention enemas or suppositories, using conventional suppository bases such as cocoa butter, other glycerides, polyethylene glycol, or a suppository wax.

The present invention also relates to a method for using the present polymyxin derivatives or a combination of such derivatives as a part of the clinical treatment of (or a preventive prophylactic regimen for) human or animal subjects suffering of an infectious disease, and comprises administering to said subject an therapeutically effective dose of at least one derivative according to the present invention, optionally in combination with an antibacterial agent.

The present invention also relates to a method of sensitizing Gram-negative bacteria to an antibacterial agent, wherein the derivative according to the present invention is administered simultaneously, or sequentially in any order, with a therapeutically effective amount of said antibacterial agent.

The derivative of the present invention and the antibacterial agent may be administered together as one formulation or by different routes. For example, the polymyxin derivative may be administered intravenously while the antibacterial agent is administered intramuscularly, intravenously, subcutaneously, orally or intraperitoneally. Alternatively, the derivative may be administered intramuscularly or intraperitoneally while the antibacterial agent is administered intravenously, intramuscularly or intraperitoneally, or the derivative may be administered in an aerosolized or nebulized form while the antibacterial agent is administered, e.g., intravenously. The derivative and the antibacterial agents may be administered simultaneously or sequentially, as long as they are given in a manner sufficient to allow both to achieve effective concentrations at the site of infection.

"Therapeutic effectiveness" is based on a successful clinical outcome, and does not require that a derivative according to the present invention, optionally in combination with an antibacterial agent, kills 100% of the bacteria involved in an infection. Successful treatment depends on achieving a level of antibacterial activity at the site of infection, sufficient to inhibit the bacteria in a manner that tips the balance in favor of the host. When host defences are maximally effective, the antibacterial effect required may be modest. Reducing organism load by even one log (a factor of 10) may permit the host's own defences to control the infection. In addition, augmenting an early bactericidal/bacteriostatic effect can be more important than long-term bactericidal/bacteriostatic effect. These early events are a significant and critical part of therapeutic success, because they allow time for host defence mechanisms to activate. Increasing the bactericidal rate may be particularly important for infections such as meningitis, bone or joint infections.

The therapeutic effectiveness of an antibacterial agent depends on the susceptibility of the bacterial species to said antibacterial agent at the clinically relevant concentration of the derivative according to this invention. The effect of compounds according to the present invention to improve the therapeutic effectiveness of antibacterial agents in vivo may be demonstrated in in vivo animal models, such as mouse peritonitis or rabbit bacteremia assays, and may be predicted on the basis of a variety of in vitro tests, including (1) determinations of the minimum inhibitory concentration (MIC) of an antibacterial agent required to inhibit growth of a Gram-negative bacterium for 24 hours, (2) determinations of the effect of an antibacterial agent on the kinetic growth curve of a Gram-negative bacterium, and (3) checkerboard assays of the MIC of serial dilutions of antibacterial agent alone or in combination with serial dilutions of compound(s). Exemplary models or tests are well known in the art.

Using in vitro determinations of MIC at 24 hours, a derivative according to the present invention may be shown to reduce the MIC of the antibacterial agent. With this result, it is expected that concurrent administration of the compound in vivo will increase susceptibiity of a Gram-negative bacterium to the antibacterial agent. A compound according to the present invention may also be shown to reduce the MIC of an antibacterial agent from the range in which the organism is considered clinically resistant to a range in which the organism is considered clinically susceptible. With this result, it is expected that concurrent administration in vivo of the one or more compound(s) according to the present invention with the antibacterial agent will reverse resistance and effectively convert the antibiotic-resistant organism into an antibiotic-susceptible organism.

By measuring the effect of antibacterial agents on the in vitro growth curves of Gram-negative bacteria, in the presence or absence of a compound according to the present invention, the compound may be shown to enhance the early antibacterial effect of antibacterial agents within a period of preferably less than 24 hours. Enhancement of early bactericidal/growth inhibitory effects is important in determining therapeutic outcome.

A polymyxin derivative according to the present invention and an antibacterial agent may also have synergistic or potentiating effects beyond the individual effects of each agent alone or the additive effects of the agents together. In a checkerboard assay, the combination of a compound according to the present invention with antibacterial agents may result in a "synergistic" fractional inhibitory concentration index (FICI). The checkerboard method is based on additivity, which assumes that the result observed with multiple drugs is the sum of the separate effects of the drugs being tested; according to this system a FICI of less than 0.5 is scored as synergy, 1 is scored as additive, and greater than 1 but less than 2 is scored as indifferent.

Antibacterial agents suitable for use in combination with derivatives according to the present invention, include e.g. macrolides, such as clarithromycin, azithromycin, and erythromycin, ketolides, lincosamines, such as clindamycin, streptogramins, rifamycins, such as rifampin, rifabutin and rifalazile, fusidic acid, mupirocin, oxazolidinones, glycopeptide antibiotics, such as vancomycin, dalbavancin, telavancin and oritavancin, fluoroquinolones, tetracycline derivatives, hydrophobic derivatives of penicillins, cephalosporins, monobactams, carbapenems, penems and other betalactam antibiotics, novobiocin, pleuromutilins, folate synthesis inhibitors, deformylase inhibitors, and bacterial efflux pump inhibitors. A person skilled in the art of treating Gram-negative infections may easily recognize additional, clinically relevant antibacterial agents that may be useful. Preferably said antibacterial agents are selected from a group of hydrophobic or moderately hydrophobic antibacterial agents against which the outer membrane of Gram-negative bacteria acts as an effective permeability barrier.

The invention also includes the use of the present compounds or combinations thereof to sensitize clinically important bacteria listed herein to the host defence mechanism complement (present in the fresh human and animal serum) by subjecting said bacteria to the action of such compounds during a clinical infection or a suspected infection. The host defence can be exerted, e.g., by the combined action of complement and polymorphonuclear leucocytes.

Those skilled in the art of medicine can readily optimize effective dosages and administration regimens for the compounds according to the present invention as well as for the antibiotics in concurrent administration, taking into account factors well known in the art including type of subject being dosed, age, weight, sex and medical condition of the subject, the route of administration, the renal and hepatic function of the subject, the desired effect, the particular compound according to the present invention employed and the tolerance of the subject to it. Dosages of all antimicrobial agents should be adjusted in patients with renal impairment or hepatic insufficiency, due to the reduced metabolism and/or excretion of the drugs in patients with these conditions. Doses in children should also be reduced, generally according to body weight.

The total daily dose of a derivative according to the present invention administered to a human or an animal can vary, for example, in amounts from 0.1 to 100 mg per kg body weight, preferably from 0.25 to 25 mg per kg body weight.

It will also be recognised by one skilled in the art that the optimal course of treatment, i.e., the number of doses given per day for a defined number of days, will be determined by the nature and extent of the condition being treated, the form, route and site of administration, and the particular patient being treated, and that such optimums can be determined by conventional techniques.

There is also provided a method for assaying a compound according to the present invention, said compound being a derivative of a natural polymyxin or octapeptin, wherein said derivative has a only 2-3 positive charges, in contrast to the naturally occurring compound from which it is derived, for antibacterial activity against a harmful Gram-negative bacterium and/or for the ability to sensitize it to antibacterial agents and/or the complement present in the serum, said method comprising the step of contacting the bacterium with said derivative of a natural polymyxin or octapeptin, and identifying derivatives possessing antibacterial activity and/or sensitizing activity towards said bacterium.

There is also provided a method to screen polymyxin and octapeptin derivatives with reduced binding to renal tissue or its constituents in or from test animals or from human origin measuring their reduced ability to competitively block the binding of aminoglycosides to the same, or block the binding of other substances known to bind to the same.

In a further aspect there is provided a method for developing novel antibiotics comprising the steps of providing a natural polymyxin or octapeptin compound, or a derivative thereof, having a total of 4 or 5 positive charges, or a total of 6 positive charges, as in deacylpolymyxins, substituting from 1 to 4 residues carrying one or more positive charges with a residue not having a positive charge, or with a covalent bond, thereby generating a polymyxin derivative having 2 or 3 positive charges, assaying said derivative compound for antibacterial activity against Gram-negative bacteria and/or for the ability to sensitize Gram-negative bacteria to an antibacterial agent, and selecting compounds having antibacterial activity against Gram-negative bacteria, or the ability to sensitize Gram-negative bacteria to an antibacterial agent.

There is also provided in accordance with the present invention a semisynthetic polymyxin derivative obtainable by treating chemically or enzymatically naturally-occurring polymyxins or octapeptins, respectively, or those variants thereof which are manufactured by genetically modified organisms. Chemical treatments include, but are not limited to, those with acetanhydride, formic acid, hydrazine, and oxalic acid. Enzymatic treatments include, but are not limited to, with enzymes such as polymyxin deacylase, ficin, papain, bromelain, subtilopeptidases, subtilisin, colistin hydrolase, and Nagarse.

Preferred compounds according to one embodiment are less cationic than natural polymyxins or octapeptins, have two (2) or three (3) positive charges only, and are:

(a) able to inhibit the growth of *Escherichia coli, Klebsiella pneumoniae, Klebsiella oxytoca, Enterobacter cloacae, Citrobacter freundii, Pseudomonas aeruginosa* or *Acinetobacter baumannii* and/or to sensitize any of them to antibiotics, and/or (b) less toxic than clinically used polymyxins, as evidenced in in vivo animal model, and/or (c) less nephrotoxic than clinically used polymyxins, as evidenced in an animal model and/or in an in vitro test that measures affinity of the compounds to kidney structures, and/or (d) able to cause less histamine liberation from the tissues than clinically used polymyxins when administered topically or when inhaled as an aerosol, and/or (e) pharmacokinetically more favorable, such as having a longer serum half life, increased renal clearance, increased urinary recovery and/or by being less inactivated by polyanionic tissue and pus constituents than clinically used polymyxins.

In a further embodiment, the compounds of the invention have one or more pharmacokinetically favorable properties as compared to native polymyxins or octapeptins (e.g., polymyxin A, polymyxin B, IL-polymyxin-$B_1$, polymyxin D, polymyxin E, polymyxin F, polymyxin M, polymyxin S, polymyxin T, circulin A, octapeptin A, octapeptin B, octapeptin C, or octapeptin D). Examples of such pharmacokinetically favorable properties include a longer serum half life, increased renal clearance, or increased urinary recovery as compared to native polymyxins or octapeptins (such as polymyxin E).

In a further embodiment, the compounds of the invention have a greater percent urinary recovery of an administered dose over 24 hours than polymyxin E (colistin). In another further embodiment, the urinary recovery, based on experiments with rats, is about 1% or greater, about 5% or greater, about 10% or greater, about 15% or greater, or about 19% or greater. In contrast, the urinary recovery of polymyxin E (colistin) was determined to be about 0.18±0.14 (Li et al., 2003), using the same dose and procedure.

In another further embodiment, the compounds of the invention have increased renal clearance as compared to polymyxin E (colistin) when administered using the same route and dosing (Li et al., 2003). In a further embodiment, the compounds of the invention have a renal clearance, based on experiments with rats, greater than about 0.1 ml/min/kg, greater than about 0.2 ml/min/kg, greater than about 0.3 ml/min/kg, greater than about 0.4 ml/min/kg, or greater than about 0.5 ml/min/kg. In another further embodiment, the renal clearance of the compounds of the invention is at least 5 times, at least 10 times, at least 20 times, at least 30 times, at least 40 times, at least 45 times, or at least 50 times that of polymyxin E (colistin), when administered at the same dose and administration route.

Methods for synthesising compounds according to the present invention include but are not limited to the following described below. For a specific compound to be synthesized, an expert in the art is able to choose the appropriate method.

1. Semisynthetic derivatives of polymyxins and octapeptins that carry an unchanged heptapeptide part and a modified acyl-aminoacyl side chain can be made by the procedures described as follows:

Protection of the free amino groups in the starting material (polymyxin or octapeptin, or modifications thereof) by methods known to those skilled in the art. The protection can be achieved by the use of residues such as t-butoxycarbonyl (tBoc), fluorenylmethoxycarbonyl (Fmoc), benzyloxycarbonyl (CBZ, Z), allyloxycarbonyl (ALOC), 3-pyridyl-N-oxide-methoxycarbonyl (as described in patent publication GB 1323962), by using Schiff bases such as benzaldehyde by the method described in Japanese Patent publication 7115630/1971 or the like which can be removed by conventional conditions compatible with the nature of the product.

In conditions where the poor water solubility occasionally poses a problem in the sub-sequent steps, the protection can be made by using negatively-charged blocking groups such as a sulfonic acid derivative of Fmoc or a carboxylic acid derivative of Fmoc, the method being described in US patent publication 2006004185. The water solubility can also be enhanced by linking a suitable, removable, negatively charged, very hydrophilic blocking group to the OH-group of threonine.

Thereafter, the compound is subjected to an enzymatic treatment with enzymes such as polymyxin deacylase, polymyxin hydrolase, papain, ficin, bromelain, subtilopeptidase, Nagarse or other enzymes that remove a terminal part of the side chain or even the entire side chain of polymyxin or octapeptin compounds. This treatment can optionally be followed by the Edman degradation procedure. The resultant compound lacks the entire side chain and consists of the cyclic heptapeptide part only, but has a free N-terminal alpha amino group.

Alternatively, polymyxins and octapeptins that have amino groups protected by benzyloxycarbonyl can be treated by oxalic acid or formic acid to yield protected deacyiderivatives, the method being described by Kurihara et al. (1974). The procedure is followed by further enzyme treatment as above and/or by Edman degradation to yield a heptapeptide.

Thereafter, a suitable residue is linked to the free alpha-amino position of the heptapeptide ring portion. The residue might contain an acyl or related residue as well as optionally amino acid residues, preferably up to three residues. For instance, one semisynthetic compound with an acyl group and two amino acid residues can be prepared by adding to the above-described heptapeptide a synthetic N-(acyl)-threonyl-D-threonyl residue. This can be achieved by conventional general techniques known to those familiar with the art of organic chemistry, these techniques including the use of N-hydroxy succinimide-linked residues as described in US 2006004185. In this particular synthesis the procedure may involve the use of 2-N-(n-octanoyl)-threonyl-D-threonyl-N-hydroxysuccinimide.

2. Acylated polymyxin nonapeptides carrying three (3) free amino groups. Polymyxin D possesses only four (4) positive charges.

The free amino groups of polymyxin D can be protected by the means described above. This is followed by an enzymatic treatment and an optional Edman degradation step, to yield a nonapeptide, which can then be acylated by acylisotiocyanate (by the method well-known to a person skilled in the art and described in US 2006004185, by acyl chloride (by the method well-known to a person skilled in the art and described in Chihara et al. 1974), or by using residues linked to N-hydroxysuccinimide (by the method well-known to a person skilled in the art and described in US 2006004185, Finally, the protective groups are removed.

In an analogous manner, acylated polymyxin S nonapeptide and acylated polymyxin F nonapeptide can be made. Both carry only three (3) free amino groups.

3. Acylated polymyxin and octapeptin heptapeptides. Heptapeptides can be made by Nagarse treatment of the natural compounds, as described by Kimura et al. 1992. Alternatively, they can be made by treatments with other enzymes such as polymyxin acylase, polymyxin hydrolase, ficin, papain, bromelain, and subtilopeptidase, followed by optional Edman degradation steps. They can also be made by deacylating the natural compounds by hydrazine or by acids such as formic acid and oxalic acid, followed by Edman degradation steps. The heptapeptide can then be acylated for instance by using the acyl chloride technique well-known to a person skilled in the art and described in Chihara et al. (1974). The acylated polymyxin heptapeptide carries only three (3) free amino groups.

4. Totally synthetic polymyxin and octapeptin derivatives can be made by the very conventional methods known for those skilled in the art. Such methods include the liquid-phase synthesis procedures as well as the solid-phase synthesis procedures described for instance by Sakura et al. (2004), Tsubery et al. (2000a, 2000b, 2002, 2005), and Ofek et al. (2004). The methods include e.g. the use of protecting agents such as Fmoc, tBoc, and CBZ at strategic positions, as well as the cyclisation step where DPPA (diphenyl phosphorazidate) or a mixture of benzotrizole-1-yl-oxy-tris-pyrrolidino-phosphonium hexafluorophosphate (PyBop), N-hydroxybenzotriazole (HoBt), and N-methylmorpholine (NMM) is used. Fmoc derivatives of many non-trivial as well as D-amino acids are commercially available.

5. Exemplary reactions related to conversion of the free amino groups to generate compounds according to the present invention having 2 or 3 positive charges may include (but are not limited to) the following reactions:

A) reaction of free amine group of the compound with a conjugation moiety comprising a reactive epoxide group, thereby generating a β-hydroxy amine linkage;

B) reaction of free amine group of the compound with a conjugation moiety comprising a reactive sulphonyl halide, thereby generating a sulfonamide linkage;

C) reaction of free amine group of the compound with a conjugation moiety comprising a reactive carboxyl acid, thereby generating an amine linkage;

D) reaction of free amine group of the compound with a conjugation moiety comprising a reactive aldehyde group (under reducing conditions), thereby generating an amine linkage;

E) reaction of free amine group of the compound with a conjugation moiety comprising a reactive ketone group (under reducing conditions), thereby generating an amine linkage;

F) reaction of free amine group of the compound with a conjugation moiety comprising a reactive isocyanate group, thereby generating a urea linkage.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

LIST OF REFERENCES

All references cited in the present application are hereby incorporated by reference in their entirety.

Chihara S, Tobita T, Yahata M, Ito A, Koyama Y. 1973. Enzymatic degradation of colistin. Isolation and identification of α-N-Acyl α,γ-diaminobutyric acid and colistin nonapeptide. Agr Biol Chem 37:2455-2463.

Chihara S, Ito A, Yahata M, Tobita T, Koyama Y. 1974. Chemical synthesis, isolation and characterization of α-N-fattyacyl colistin nonapeptide with special reference to the correlation between antimicrobial activity and car-bon number of fattyacyl moiety. Agric Biol Chem 38:521-529.

de Visser P C, Kriek N M A J, van Hooft P A V, Van Schepdael A, Filippov D V, van der Marel G A, Overkleeft H S, van Boom J H, Noort D. 2003. Solid-phase synthesis of polymyxin $B_1$ and analogues via a safety-catch approach. J. Peptide Res. 61:298-306.

Kimura Y, Matsunaga H, Vaara M. 1992. Polymyxin B octapeptide and polymyxin B heptapeptide are potent outer membrane permeability-increasing agents. J Antibiot 45:742-749.

Kurihara T, Takeda H, Ito H, Sato H, Shimizu M, Kurosawa A. 1974. Studies on the compounds related to colistin. IX. On the chemical deacylation of colistin and colistin derivatives. Yakugaku Zasshi 94:1491-1494.

Li J, Milne R W, Nation R L, Turnidge J B, Coulthard K, and Johnson D W. 2001. A simple method for the assay of colistin in human plasma, using pre-column derivatization with 9-fluorenylmethyl chloroformate in solid-phase extraction cartridges and reversed-phase high-performance liquid chromatography. J Chromatogr B Biomed Sci Appl 761:167-175.

Li J, Milne R W, Nation R L, Turnidge J B, Smeaton T C, and Coulthard K. 2003. Use of high-performance liquid chromatography to study the pharmacokinetics of colistin sulfate in rats following intravenous administration. Antimicrob Agents Chemother 47:1766-1770.

Li J, Milne R W, Nation R L, Turnidge J B, Smeaton T C, and Coulthard K. 2004. Pharmacokinetics of colistin methanesulphonate and colistin in rats following an intravenous dose of colistin methanesulphonate. J Antimicrob Chemother 53:837-840.

Nagai J, Saito M, Adachi Y, Yumoto R, Takano M. 2006. Inhibition of gentamicin binding to rat renal brush-border membrane by megalin ligands and basic peptides. J Control Release 112:43-50.

Nikaido H. 2003. Molecular basis of bacterial outer membrane permeability revisited. Microbiol. Molec Biol Rev 67:593-656.

Nikaido H, Vaara M. 1985. Molecular basis of bacterial outer membrane permeability. Microbiol. Rev 49:1-32.

Okimura K, Ohki K, Sato Y, Ohnishi K, Uchida Y, Sakura N. 2007. Chemical conversion of natural polymyxin B and colistin to their N-terminal derivatives. Bull. Chem. Soc. Jpn. 80 (No. 3):543-552.

Rose F, Heuer K U, Sibelius U, Hombach-Klonisch S, Ladislau K, Seeger W, Grimminger F. 1999. Targeting lipopolysaccharides by the non-toxic polymyxin B nonapeptide sensitizes resistant *E. coli* to the bactericidal effect of human neutrophils. J Infect Dis 182:191-199.

Sakura N, Itoh T, Uchida Y, Ohki K, Okimura K, Chiba K, Sato Y, Sawanishi H. 2004. The contribution of the N-terminal structure of polymyxin B peptides to antimicrobial and lipopolysaccharide binding activity. Bull Chem Soc Jpn 77:1915-1924.

Srinivasa B D, Ramachandran L K. 1978. Chemical modification of peptide antibiotics: Part VI—Biological activity of derivatives of polymyxin B. Ind Biochem Biophys 14:54-58.

Srinivasa B D, Ramachandran L K. 1979. The polymyxins. J Scient Industr Res 38:695-709.

Srinivasa B D, Ramachandran L K. 1980. Essential amino groups of polymyxin B. Ind J Biochem Biophys 17:112-118.

Storm D R, Rosenthal K S, Swanson P E. 1977. Polymyxin and related peptide antibiotics. Annu Rev Biochem 46:723-63.

Teuber M. 1970. Preparation of biologically active mono-N-acetyl(14C)-derivatives of the membrane-specific polypeptide antibiotic polymyxin B. Z Naturforsch 25b: 117.

Tsubery H, Ofek I, Cohen S, Fridkin M. 2000a. Structure-function studies of polymyxin B nonapeptide: Implications to sensitization of Gram-negative bacteria. J. Med Chem 43:3085-3092.

Tsubery H, Ofek I, Cohen S, Fridkin M. 2000b. The functional association of polymyxin B with bacterial lipopolysaccharide is stereospecific: Studies on polymyxin B nonapeptide. Biochemistry 39:11837-11844.

Tsubery H, Ofek I, Cohen S, Fridkin M. 2001. N-terminal modifications of polymyxin B nonapeptide and their effect on antibacterial activity. Peptides 22:1675-1681.

Tsubery H, Ofek I, Cohen S, Eisenstein M, Fridkin M. 2002. Modulation of the hydro-phobic domain of polymyxin B nonapeptide: effect on outer-membrane permeabilization and lipopolysaccharide neutralization. Molecular Pharmacology 62:1036-42.

Tsubery H, Yaakov H, Cohen S, Giterman T, Matityahou A, Fridkin M, Ofek I. 2005. Neopeptide antibiotics that function as opsonins and membrane-permeabilizing agents for gram-negative bacteria. Antimicrob Agents Chemother 49:3122-3128.

Vaara M. 1992. Agents that increase the permeability of the outer membrane. Microbiol. Rev 56:395-411.

Vaara M. 1993. Antibiotic-supersusceptible mutants of *Escherichia coli* and *Salmonella typhimurium*. Antimicrob Agents Chemother 37:2255-2260.

Vaara M, Vaara T. 1983a. Sensitization of Gram-negative bacteria to antibiotics and complement by a nontoxic oligopeptide. Nature (London) 303:526-528.

Vaara M, Vaara T. 1983b. Polycations sensitize enteric bacteria to antibiotics. Antimicrob Agents Chemother 24:107-113.

Vaara M, Vaara T. 1983c. Polycations as outer membrane-disorganizing agents. Antimicrob Agents Chemother 24:114-122.

Vaara M, Viljanen P, Vaara T, Mäkelä P. 1984. An outer membrane disorganizing peptide PMBN sensitizes *E. coli* strains to serum bactericidal action. J Immunol 132:2582-2589.

Viljanen P, Matsunaga H, Kimura Y, Vaara M. 1991. The outer membrane permeability-increasing action of deacylpolymyxins. J Antibiotics 44:517-523.

EXAMPLES

The following examples illustrate certain embodiments of the present invention and should not be construed as limiting the scope of the invention.

Example 1

Peptide Synthesis

Polymyxin derivatives ("NAB peptides" or "NAB compounds") were synthesized by conventional solid phase chemistry, using the standard Fmoc protection strategy. The amino acid at the C-terminus is commercially available as pre-attached to the solid phase and when cleaved off the resin with acid, yields a C-terminal carboxylic acid.

The strategy in the protection was to use three levels of orthogonal protection, temporary Fmoc protection for the alpha amino functions, groups which are removed during the acid cleavage stage, and semi-permanent protection to cover reactive side chain functions while the cyclisation reaction takes place. After cleavage of the peptide from the resin, the C-terminal carboxylic acid is reacted with an amino function on the side chain of one of the amino acids to form a cyclic peptide. After the cyclisation step, the semi-permanent protection groups are removed to yield NAB peptide.

Accordingly, the alpha amino function of the amino acid was protected by fluorenyl-methoxycarbonyl (Fmoc) and Fmoc was removed by 20% piperidine in DMF at every cycle. The amino acid that is involved with cyclisation, i.e., diaminobutyric acid, was protected by t-butoxycarbonyl (tBoc), an acid labile group which was removed at the cleavage step. All the other amino acids which have functional side chain groups were protected by a group that is stable to the acid cleavage stage, i.e., benzyloxycarbonyl (Z). Amino acids phenylalanine and leucine naturally needed no side chain protection. The amino terminus was not protected; this enabled direct reaction in the acylation procedure.

The synthesis steps were performed in a commercial automated synthesizer that employed O-(6-Chlorobenzotriazol-1-yl)-N,N,N',N'-tetramethyluronium hexafluorophosphate (HCTU) as activator.

6-methylheptanoic acid (6-MHA) was from Ultra Scientific Inc, North Kingstown, R.I., USA (product number, FLBA 002). Other fatty acids were from a standard supplier.

The acylation was performed by using a four-fold molar excess of each amino acid or the fatty acid, four-fold molar excess of the activator HCTU (see above), and an eight-fold molar excess of N-methyl morpholine. The reaction time was 30 min.

The amino acids were purchased already protected from a standard supplier. The peptide was removed from the resin by reaction with a solution of 95% trifluoroacetic acid and 5% water for 2 hours at room temperature, to yield the partially protected product. The resulting peptide was precipitated with diethyl ether.

The cyclisation mixture used was benzotriazole-1-yl-oxy-tris-pyrrolidino-phosphonium hexafluorophosphate (PyBop), N-hydroxybenzotriazole (HoBt), and N-methyl morpholine (NMM) at the molar excess of 2, 2, and 4, respectively. The peptide was dissolved in dimethylformamide, the cyclisation mix was added and allowed to react for 2 hours. The cyclised, protected peptide was precipitated by the addition of cold diethyl ether. Any residual PyBop was removed by washing the peptide with water.

The remaining side chain protection groups (Z) were removed by catalytic dehydrogenation. The peptide was dissolved in acetic acid-methanol-water (5:4:1), under an atmosphere of hydrogen and in the presence of a palladium charcoal catalyst.

The peptide was purified by reverse phase chromatography using conventional gradients of acetonitrile:water:trifluoroacetic acid. The product was dried by lyophilisation.

The yield was 20-40 mg representing approx. 20%-40% of the theoretical, calculated from the molar amount (approx. 100 micromoles) of the first amino acyl residue bound to the resin.

The purity, as estimated by reversed phase HPLC was more than 95%. For acylated peptides, the Edman degradation product did not reveal any amino acid residue, indicating that the α-amino group of the N-terminal amino acid residue was blocked, as expected, due to the successful N-acylation. Within experimental error, the masses obtained were those expected from the theoretical values.

Example 2

Direct Antibacterial Activity of the Compounds Against *Escherichia coli*

Peptides synthesized in Example 1, all carrying at least two (2) but not more than three (3) positive charges, were studied for their ability to inhibit the growth of *E. coli*. This was tested employing LB agar (LB Agar Lennox, Difco, BD, Sparks, Md., U.S.A) plates. The indicator organism *E. coli* IH3080 (K1:O018) was an encapsulated strain originally isolated from a neonate suffering from meningitis (Vaara et al. 1984) and obtained from National Public Health Institute, Helsinki, Finland.

From an overnight-grown culture of IH3080 on LB agar, a suspension of approx. $10^8$ cells/ml was prepared in 0.9% NaCl. Aliquots of this suspension were then pipetted on the agar plates and the plates were gently shaken to spread the suspension evenly on the entire surface of the plate. Thereafter, the unabsorbed part of the suspension was removed by using a Pasteur pipette. After the surface had dried, small wells (diameter, 2 mm) were drilled on the plates (five wells per plate) by using a sterile sharp-edged narrow metal tube, single-use pipette tip, and vacuum suction. An alternative method used a swab to spread the inoculum. Samples (4 μl and 10 μl) of the peptide solution in 0.9% NaCl (at concentrations of 1 μg/ml and 0.1 μg/ml) were then pipetted to the wells and the sample fluids were allowed to absorb. Controls included 0.9% NaCl solution without the compound to be tested. The plates were then incubated for 18 h at 37° C. whereafter the diameters of growth inhibition zones around each well were measured; the diameter of the well itself was not reduced. Finally, the diameters were converted to surface areas of growth inhibition (in square mm).

Table 2 shows the antibacterial activity of the derivatives against *E. coli* IH3080 as compared with that of an equal amount of polymyxin B as well as of some polymyxin derivatives not related to the present invention. NAB734, NAB737, NAB739, NAB740, NAB748 and NAB749 were the most antibacterial compounds and were even more antibacterial than polymyxin B against *E. coli* IH3080. A well containing 4 μg of NAB739 produced a growth inhibition area as wide as 133 square mm. In all these NAB compounds, the side chain consists of two amino acyl residues that carry hydroxyl groups.

Unlike NAB739, NAB7061 was not antibacterial at 4 μg. However, it displayed notable antibacterial activity at 10 μg. NAB7061 differs from NAB739 only by carrying Abu (instead of DSer) in R3. Prolonging the length of the fatty acyl part from C8 in NAB7061 to C10 in NAB7062 resulted in notably enhanced antibacterial activity manifesting at 4 μg. In addition, three other peptides (NAB738, NAB716 and NAB719) displayed notable antibacterial activity, albeit clearly weaker than NAB739 and the other most antibacterial compounds.

A common property of the compounds directly antibacterial to *E. coli* was the presence of three positive charges out of which either all the three or at least two were located in suitable positions in the cyclic part. In the latter case the relative positions of said charges significantly affected the potency of the antibacterial activity against *E. coli*.

Furthermore, as shown in the Table 2, also the structure and length of the side chain has significant influence on the potency of the antibacterial activity. The presence of a side chain consisting of at least two amino acyl residues appears to be important for the compounds antibacterial against *E. coli*, since the compounds lacking either $R^2$ (NAB713) or both $R^2$ and $R^3$ (octanoyl PBHP) also lacked the direct antibacterial activity in the conditions used in the assay. However, it can be anticipated, that the lack of those residues can be compensated by using instead of octanoyl residue, a more extended residue as the R(FA).

TABLE 2

Structure of the compounds and their antibacterial activity* against *Escherichia coli* IH3080

| | Structure** | | | | |
|---|---|---|---|---|---|
| | | Peptide sequence*** | | Positive Charges in | Antibacterial Activity at |
| | FA-part | side chain | cyclic part | cyclic part / total | 4 μg / 10 μg |
| Reference compounds | | | | | | |
| Polymyxin B | MO(H)A | XTX | cy[XXFLXXT] | 3 | 5 | 79 | 133 |
| Colistin (polymyxin E) | MO(H)A | XTX | cy[XXLLXXT] | 3 | 5 | ND | ND |
| Deacylpolymyxin B | — | +XTX | cy[XXFLXXT] | 3 | 6 | 57 | 113 |
| Deacylcolistin Polymyxin B | — | +XTX | cy[XXLLXXT] | 3 | 6 | 79 | 95 |

TABLE 2-continued

Structure of the compounds and their antibacterial activity* against *Escherichia coli* IH3080

| | Structure** | | | Positive Charges in | | Antibacterial Activity at | |
|---|---|---|---|---|---|---|---|
| | FA-part | Peptide side chain | sequence*** cyclic part | cyclic part | total | 4 µg | 10 µg |
| nonapeptide Polymyxin B | — | +TX | cy[XX<u>F</u>LXXT] | 3 | 5 | 0 | 0 |
| heptapeptide | — | — | +cy[XX<u>F</u>LXXT] | 4 | 4 | 0 | 0 |
| NAB 704 | — | +TZ | cy[XX<u>F</u>LXXT] | 3 | 4 | 0 | 0 |
| NAB 705 | — | +ZTZ | cy[XX<u>F</u>LXXT] | 3 | 4 | 0 | 0 |
| Octanoyl PMBH | OA | — | cy[XX<u>F</u>LXXT] | 3 | 3 | 0 | 0 |
| Cpds of the present invention | | | | | | | |
| NAB 739 | OA | T<u>S</u> | cy[XX<u>F</u>LXXT] | 3 | 3 | 133 | 177 |
| NAB 740 | DA | T<u>S</u> | cy[XX<u>F</u>LXXT] | 3 | 3 | 95 | 133 |
| NAB 737 | OA | T<u>T</u> | cy[XX<u>F</u>TXXT] | 3 | 3 | 133 | 201 |
| NAB 734 | OA | T<u>S</u> | cy[XX<u>F</u>TXXT] | 3 | 3 | 113 | 177 |
| NAB 7062 | DA | TZ | cy[XX<u>F</u>LXXT] | 3 | 3 | 50 | 99 |
| NAB 7061 | OA | TZ | cy[XX<u>F</u>LXXT] | 3 | 3 | 0 | 50 |
| NAB 706 | MHA | TZ | cy[XX<u>F</u>LXXT] | 3 | 3 | 5 | 7 |
| NAB 707 | MHA | ZTZ | cy[XX<u>F</u>LXXT] | 3 | 3 | 5 | 7 |
| NAB 716 | OA | TX | cy[XX<u>F</u>LZXT] | 2 | 3 | 13 | 64 |
| NAB 719 | OA | TZ | cy[XX<u>F</u>LXXL] | 3 | 3 | 7 | 50 |
| NAB 738 | OA | T<u>A</u> | cy[XX<u>F</u>TXXT] | 3 | 3 | 0 | 64 |
| NAB 717 | OA | TX | cy[XX<u>F</u>LXZT] | 2 | 3 | 0 | 0 |
| NAB 718 | OA | TZ | cy[XX<u>L</u>LXXT] | 3 | 3 | 0 | 0 |
| NAB 733 | OA | <u>AA</u> | cy[XX<u>F</u>LXXT] | 3 | 3 | 0 | 0 |
| NAB 736 | DA | — | cy[XX<u>F</u>LXXT] | 3 | 3 | 0 | 0 |
| NAB 713 | OA | Z | cy[XX<u>F</u>LXXT] | 3 | 3 | 0 | 0 |
| NAB 715 | OA | TX | cy[X<u>ZF</u>LXXT] | 2 | 3 | 0 | 0 |
| NAB 721 | MHA | XTX | cy[XX<u>F</u>LZZT] | 1 | 3 | 0 | 0 |
| NAB 731 | OA | TZ | cy[X<u>K</u>FLXXT] | 3 | 3 | 0 | 0 |
| NAB 710 | OA | TZ | cy[XZ<u>F</u>LXXT] | 2 | 2 | 0 | 7 |
| NAB 709 | OA | TZ | cy[XX<u>F</u>LXZT] | 2 | 2 | 0 | 0 |
| NAB 708 | OA | TZ | cy[XX<u>F</u>LZXT] | 2 | 2 | 0 | 0 |
| NAB 725 | OA | XTX | cy[XZ<u>F</u>LXZT] | 1 | 3 | 0 | 0 |
| NAB 726 | OA | XTX | cy[XZ<u>F</u>LZXT] | 1 | 3 | 0 | 0 |
| NAB 722 | MHA | XTX | cy[XZ<u>F</u>LZZT] | 0 | 2 | 0 | 0 |
| NAB 735 | OA | XXX | cy[XZ<u>F</u>LZZT] | 0 | 3 | 0 | 0 |
| NAB 701 | — | +TX | cy[XX<u>F</u>LZZT] | 1 | 3 | 0 | 0 |
| NAB 702 | — | +TX | cy[XX<u>F</u>LBBT] | 1 | 3 | 0 | 0 |

TABLE 2-continued

Structure of the compounds and their antibacterial activity* against *Escherichia coli* IH3080

| | Structure** | | | Positive Charges in | | Antibacterial Activity at | |
|---|---|---|---|---|---|---|---|
| | FA-part | Peptide side chain | sequence*** cyclic part | cyclic part | total | 4 µg | 10 µg |
| NAB 703 | — | +TX | cy[XXFLJJT] | 1 | 3 | 0 | 0 |
| NAB 743 | OA | TS | cy[XXFLXXT] | 3 | 3 | 38 | 79 |
| NAB 746 | OA | TN | cy[XXFLXXT] | 3 | 3 | 0 | 13 |
| NAB 748 | OA | TT*S* | cy[XXFLXXT] | 3 | 3 | 113 | 156 |
| NAB 749 | OA | AT*S* | cy[XXFLXXT] | 3 | 3 | 113 | 158 |

*Antibacterial activity measured as the growth inhibition (in square millimeters) around a well containing 4 or 10 microgram of a compound on LB plates
**One-letter codes for amino acyl residues: A, Ala; F, Phe; K, Lys; L, Leu; S, Ser; T, Thr; X Dab; Z, Abu; B, N-γ-formyl-Dab; J, N-γ-acetyl-Dab.
Underlined letters indicate residues that are in D-configuration.
Bold letters indicate residues that carry a positive charge.
Bold + indicates the positive charge of the α-amino group in the free N-terminus of the peptide.
Abbreviation: cy, cyclo.
***In the sequence listing X, Z, B and J are denoted Xaa, and defined as modified residues (MOD_RES).

Example 3

Direct Antibacterial Activity of Selected Nab Compounds Against *Acinetobacter baumannii* and *Pseudomonas aeruginosa*

Direct antibacterial activity of sixteen NAB compounds against *Acinetobacter baumannii* ATCC 19606 and *Pseudomonas aeruginosa* ATCC 27853 was tested by using the susceptibility determination method described in Example 2. The results are shown in Table 3. Five compounds (NAB7062, NAB734, NAB737, NAB739, and NAB740) had very notable activity against *A. baumannii*. In Example 2, the same compounds were shown to be very potent against *E. coli*. The antibacterial activity of NAB739 and NAB740 were as strong as or even stronger than that of polymyxin B.

Against *P. aeruginosa*, the most active NAB compounds were NAB739, NAB740 as well as NAB736, which is quite inactive against *E. coli* and *Acinetobacter baumannii*. NAB740 was the most active compound and its activity was as strong as that of polymyxin B. All the three NAB compounds lack positive charges in the side chain and were still active against *P. aeruginosa*. This finding is against the conclusion of Srinivasa and Ramachandran (1980a) that the free amino groups in R1 and R3 are essential for the growth inhibition of *P. aeruginosa*.

Surprisingly, NAB736 is rather effective against *P. aeruginosa* whereas octanoyl PMBH is much less effective. Accordingly, lengthening the R(FA) part from C8 to C10 has a marked effect on the activity.

TABLE 3

Antibacterial activity* of sixteen (16) novel compounds against *Acinetobacter baumannii* and *Pseudomonas aeruginosa*

| | *A. baumannii* 4 µg | ATCC 19606 10 µg | *Ps. aeruginosa* 4 µg | ATCC 27853 10 µg |
|---|---|---|---|---|
| NAB 7061 | 0 | 0 | 0 | 0 |
| NAB 7062 | 13 | 38 | 0 | 0 |
| NAB 716 | 0 | 0 | 0 | 0 |
| NAB 717 | 0 | 0 | 0 | 0 |
| NAB 718 | 0 | 0 | 0 | 0 |
| NAB 719 | 0 | 0 | 0 | 0 |
| NAB 736 | 0 | 0 | 38 | 79 |
| NAB 734 | 38 | 95 | 13 | 50 |
| NAB 737 | 38 | 79 | 0 | 28 |
| NAB 738 | 0 | 0 | 0 | 0 |
| NAB 739 | 113 | 177 | 38 | 79 |
| NAB 740 | 133 | 201 | 64 | 133 |
| NAB 743 | 0 | 0 | 28 | 38 |
| NAB 746 | 0 | 0 | 0 | 20 |
| NAB 748 | 20 | 50 | 20 | 50 |
| NAB 749 | 20 | 38 | 20 | 28 |
| Polymyxin B | 113 | 154 | 95 | 133 |
| PMBN | 0 | 0 | 113 | 177 |
| Octanoyl PMBH | nd | nd | 0 | 13 |

*Antibacterial activity measured as the growth inhibition (in square millimeters) around a well containing 4 or 10 µg of the compound on LB plates Example 4

Direct Antibacterial Activity of NAB734 Against Selected Gram-Negative Bacteria

The susceptibility of eleven Gram-negative bacterial strains (nine different species) to NAB734 and polymyxin B was compared by using the susceptibility determination method described in Example 2. The strains included those belonging to the species of *Serratia marcescens* and *Proteus mirabilis*, both species generally known to be resistant to polymyxin. Furthermore, the susceptibility determination was also performed by using the Gram-positive bacterium, *Staphylococcus aureus*, also generally known to be polymyxin-resistant. Ten of the strains originated from ATCC (American Type Culture Collection, Manassas, Va., U.S.A.), and one from CCUG (Culture Collection of University of Gothenburg, Sweden). The source of *E. coli* IH3080 has been described in Example 2. Polymyxin B sulfate was from Sigma-Aldrich (St. Louis, Mo., USA).

The results in Table 4 show that NAB734 can be generally regarded to be approximately as potent as polymyxin B against *E. coli, Klebsiella pneumoniae, Klebsiella oxytoca, Enterobacter cloacae*, and *Citrobacter freundii*. It appears to be somewhat less potent than polymyxin B against *Acinetobacter baumannii* and clearly less potent than polymyxin B against *Pseudomonas aeruginosa*. Representatives of known polymyxin-resistant bacterial species were resistant to NAB734 also. This suggests that NAB734 has a very specific antibacterial action and that its mode of action is quite similar to that of polymyxin B.

TABLE 4

Antibacterial activity* of NAB 734 against selected Gram-negative bacteria and *Staphylococcus aureus*

| Strain | NAB 734 | | Polymyxin B sulfate | |
|---|---|---|---|---|
| | 4 µg | 10 µg | 4 µg | 10 µg |
| *E. coli* ATCC25922 | 133 | 177 | 95 | 133 |
| *E. coli* IH3080 | 113 | 154 | 95 | 133 |
| *K. pneumoniae* ATCC13883 | 64 | 113 | 79 | 113 |
| *K. pneumoniae* CCUG45421 | 64 | 104 | 95 | 133 |
| *K. oxytoca* ATCC13182 | 95 | 143 | 79 | 104 |
| *E. cloacae* ATCC23355 | 133 | 177 | 95 | 143 |
| *C. freundii* ATCC8090 | 133 | 177 | 95 | 154 |
| *A. baumannii* ATCC19606 | 57 | 79 | 113 | 154 |
| *P. aeruginosa* ATCC27853 | 13 | 50 | 95 | 133 |
| *S. marcescens* ATCC8100 | 0 | 0 | 0 | 0 |
| *P. mirabilis* ATCC29906 | 0 | 0 | 0 | 0 |
| *S. aureus* ATCC 25923 | 0 | 0 | 0 | 0 |

*Antibacterial activity measured as the growth inhibition (in square millimeters) around wells containing 4 or 10 µg of the compound on LB plates Example 5

The Ability of the NAB Compounds to Sensitize *E. coli* IH3080 to a Model Antibiotic Rifampin Novel NAB peptides according to the present invention and all carrying at least two (2) but not more than three (3) positive charges, were also studied for their ability to sensitize *E. coli* IH3080 to rifampin. This was tested in parallel with the susceptibility determinations described in Example 2 and by employing LB plates that contain increasing concentrations (0.1 µg/ml, 0.3 µg/ml, 1 µg/ml) of rifampin (Sigma-Aldrich, St. Louis, Mo., U.S.A).

Table 5 shows the activity of the NAB compounds (4 µg) against *E. coli* IH3080 in the presence of rifampin (0.1 and 1 µg/ml) as compared with the activity of an equal amount of previously described substances known to sensitize Gram-negative bacteria to antibacterial agents, i.e., polymyxin B heptapeptide, deacylpolymyxin B, deacylcolistin, polymyxin B nonapeptide, as well as with polymyxin B. The compounds also included octanoyl PMBH, an agent that has not previously been reported to be able to sensitize bacteria to antibiotics.

Several NAB compounds sensitized *E. coli* IH3080 to the antibacterial effect of as low a concentration of rifampin as 0.1 µg/ml. In the absence of the compounds tested, a hundred-fold concentration (10 µg/ml) of rifampin was needed for the inhibitory effect. Several compounds that lacked a notable direct antibacterial activity at 4 µg were able to sensitize the target bacterium to rifampin. Such compounds included NAB7061, NAB717, NAB718, NAB733 and NAB 746.

Furthermore, most of the NAB compounds that had direct antibacterial activity, i.e., antibacterial activity in the absence of rifampin (see Example 2), inhibited the target bacterium even more effectively in the presence of rifampin. The ability of the most active compounds, such as NAB734, NAB737, NAB738, NAB739, NAB743, NAB748, and NAB749, was clearly even better than that of PMBN, the well-known effective permeabilizer of the OM.

The most active NAB compounds carry three (3) positive charges and have at least two (2) positive charges suitably positioned in the cyclic part, the relative positioning of which affecting the potency of the sensitizing activity. It should indeed be noted, that NAB716, that carries only two positive charges in the cyclic part and has the third positive charge in the form of a Dab residue in R3, is notably able to sensitize *E. coli* to rifampin.

Amongst the series of compounds all having octanoyl residue as R(FA), octanoyl PMHP, that lacks both R2 and R3, possessed the weakest sensitizing activity, NAB713, that lacks R2, possessed a somewhat better activity, and NAB7061, that possesses both R2 and R3 had a remarkable activity. This indicates that the presence of R2 and R3 is advantageous. However, their absence can be at least partially compensated by lengthening the R(FA) part as in NAB736. It carries decanoyl residue as the R(FA) part, lacks both R2 and R3, and is quite active as a sensitizer.

NAB compounds that carry both of their two (2) positive charges in the cyclic part were less active than the structurally otherwise analogous NAB compounds that carry all of their three (3) positive charges in the cyclic part, or, for one compound (NAB708), inactive in the study conditions employed.

NAB compounds that carry two (2) positive charges in the side chain and one (1) positive charge in the cyclic part have very modest, if any activity, in the study conditions employed. NAB735, that carries all of its three (3) positive charges in the side chain is inactive in the study conditions employed. Again the relative positions of the said charges in the cyclic part affected the potency of the sensitizing activity.

TABLE 5

Antibacterial activity of the compounds (4 µg) against *E. coli* IH3080 in the presence of rifampin*

| | Antibacterial activity in the presence of rifampin concn (µg/ml) of | | |
|---|---|---|---|
| | 0 | 0.1 | 1.0 |
| Reference and other compounds | | | |
| Polymyxin B | 79 | 95 | 104 |
| Colistin (polymyxin E) | ND | ND | ND |
| Deacylpolymyxin B | 57 | 79 | 127 |
| Deacylcolistin | 79 | 87 | 127 |
| Polymyxin B nanapeptide | 0 | 20 | 113 |
| Polymyxin B heptapeptide | 0 | 0 | 38 |
| NAB 704 | 0 | 0 | 24 |
| NAB 705 | 0 | 0 | 5 |
| Octanoyl PMBH | 0 | 0 | 38 |
| Novel compounds of the present invention | | | |
| NAB 739 | 133 | 177 | 201 |
| NAB 740 | 95 | 95 | 95 |
| NAB 737 | 133 | 177 | 201 |
| NAB 734 | 113 | 154 | 201 |
| NAB 7062 | 50 | 104 | 104 |
| NAB 7061 | 0 | 113 | 155 |

TABLE 5-continued

Antibacterial activity of the compounds (4 μg) against
E. coli IH3080 in the presence of rifampin*

| | Antibacterial activity in the presence of rifampin concn (μg/ml) of | | |
|---|---|---|---|
| | 0 | 0.1 | 1.0 |
| NAB 706 | 5 | 79 | 133 |
| NAB 707 | 5 | 87 | 113 |
| NAB 716 | 13 | 133 | 165 |
| NAB 719 | 7 | 79 | 95 |
| NAB 738 | 0 | 133 | 177 |
| NAB 717 | 0 | 71 | 95 |
| NAB 718 | 0 | 13 | 133 |
| NAB 733 | 0 | 95 | 113 |
| NAB 736 | 0 | 113 | 133 |
| NAB 713 | 0 | 20 | 38 |
| NAB 715 | 0 | 0 | 33 |
| NAB 721 | 0 | 13 | 28 |
| NAB 731 | 0 | 0 | 5 (22**) |
| NAB 710 | 0 | 7 | 13 |
| NAB 709 | 0 | 0 | 13 |
| NAB 708 | 0 | 0 | 0 |
| NAB 725 | 0 | 0 | 0 |
| NAB 726 | 0 | 0 | 0 |
| NAB 722 | 0 | 0 | 0 |
| NAB 735 | 0 | 0 | 0 |
| NAB 701 | 0 | 0 | 0 |
| NAB 702 | 0 | 0 | 0 |
| NAB 703 | 0 | 0 | 0 |
| NAB 743 | 38 | 133 | 227 |
| NAB 746 | 0 | 79 | 95 |
| NAB 748 | 113 | 154 | 154 |
| NAB 749 | 133 | 133 | 177 |

*Antibacterial activity measured as the growth inhibition (in square millimeters) around a well containing 4 μg of a compound on plates with no rifampin or rifampin (0.1 or 1.0 μg/ml)
**The value in parentheses was obtained using a well containing 10 μg of the compound Example 6

The Ability of the NAB Compounds to Sensitize Acinetobacter baumannii and Pseudomonas Aeruginosa to a Model Antibiotic Rifampin NAB peptides related to present invention were also studied for their ability to sensitize A. baumannii and P. aeruginosa to rifampin (Table 6). This was tested in parallel with the susceptibility determinations described in Example 3 and by employing LB plates that contain increasing concentrations (0.1 μg/ml, 0.3 μg/ml, 1 μg/ml) of rifampin.

Several NAB compounds possessed a very marked ability to sensitize A. baumannii to rifampin. The ability of the most active compounds NAB734, NAB737, and NAB739 was clearly even better than that of PMBN, the well-known effective permeabilizer of the OM. NAB739 inhibited the growth of P. aeruginosa somewhat better in the presence of rifampin than in its absence.

TABLE 6

Antibacterial activity* of sixteen (16) novel compounds (4 μg) against Acinetobacter baumannii and Pseudomonas aeruginosa in the presence of rifampin (0.1 or 0.3 μg/ml)

| | A. baumannii ATCC 19606 | | | Ps. aeruginosa ATCC 27853 | | |
|---|---|---|---|---|---|---|
| | 0 | 0.1 | 0.3 | 0 | 0.1 | 0.3 |
| NAB 7061 | 0 | 28 | 50 | 0 | 0 | 0 |
| NAB 7062 | 13 | 50 | 95 | 0 | 0 | 7 |
| NAB 716 | 0 | 0 | 64 | 0 | 0 | 0 |
| NAB 717 | 0 | 0 | 50 | 0 | 0 | 0 |

TABLE 6-continued

Antibacterial activity* of sixteen (16) novel compounds (4 μg) against Acinetobacter baumannii and Pseudomonas aeruginosa in the presence of rifampin (0.1 or 0.3 μg/ml)

| | A. baumannii ATCC 19606 | | | Ps. aeruginosa ATCC 27853 | | |
|---|---|---|---|---|---|---|
| | 0 | 0.1 | 0.3 | 0 | 0.1 | 0.3 |
| NAB 718 | 0 | 0 | 38 | 0 | 0 | 0 |
| NAB 719 | 0 | 154 | 133 | 0 | 0 | 7 |
| NAB 736 | 0 | 95 | 154 | 38 | 38 | 38 |
| NAB 734 | 38 | 201 | 283 | 13 | 20 | 20 |
| NAB 737 | 38 | 201 | 283 | 0 | 20 | 20 |
| NAB 738 | 0 | 95 | 154 | 0 | 13 | 13 |
| NAB 739 | 113 | 177 | 314 | 38 | 64 | 64 |
| NAB 740 | 133 | 154 | 154 | 64 | 64 | 64 |
| NAB 743 | 0 | 38 | 227 | 28 | 28 | 28 |
| NAB 746 | 0 | 64 | 95 | 0 | 7 | 0 |
| NAB 748 | 20 | 133 | 201 | 20 | 13 | 20 |
| NAB 749 | 20 | 154 | 201 | 20 | 20 | 13 |
| PMBN | 0 | 133 | 154 | 113 | 113 | 154 |
| Octanoyl PMBH | nd | nd | nd | 0 | 13 | 13 |

*Antibacterial activity measured as the growth inhibition (in square millimeters) around a well containing 4 μg of a compound on plates with no rifampin (control) or with rifampin (0.1 or 0.3 μg/ml)

Example 7

NAB7061 Sensitizes E. Coli, Klebsiella pneumoniae, and Enterobacter cloacae to a Broad Range of Antibacterial Agents The minimum inhibitory concentrations (MIC) of a representative set of clinically used antimicrobial agents were determined for two strains of E. coli (ATCC25922 and IH3080), K. pneumoniae ATCC13883, and E. cloacae ATCC23355 by using Mueller-Hinton agar medium (product no LabO39; LabM Ltd., Bury, Lancs, U.K.) in the presence of NAB7061 (4 μg/ml) as well as in its absence. MICs were determined by using E-strips (Biodisk Ltd., Solna, Sweden) according to the manufacturer's instructions. The NAB7061 concentration used did not itself inhibit the growth of the target bacteria. The MIC of NAB7061 for E. coli IH3080 and K. pneumoniae ATCC13883 was >16 μg/ml, for E. coli ATCC25922 16 μg/ml, and for E. cloacae ATCC23355 8 μg/ml.

The results are shown in Table 7. NAB7061 at a concentration of 4 μg/ml was able to sensitize the tested strains to rifampin by a factor ranging from 170 to 1500. Sensitization factor is defined as the ratio of the MIC of an antibiotic in the absence of NAB7061 to that in the presence of 4 μg/ml of NAB7061. Extremely high sensitization factors were observed also to clarithromycin (63-380), mupirocin (24-512), azithromycin (31-94), erythromyxin (21-48), and for some of the strains, to fusidic acid, quinupristin-dalfopristin, clindamycin, linezolid, and vancomycin. All these antibacterial agents are notably hydrophobic or large (vancomycin) and are known to be excluded by the intact OM of Gram-negative bacteria but penetrate the damaged OM. No significant sensitization (sensitization factor <2, tested by using E. coli ATCC25922) was found to piperacillin, ceftazidime, cefotaxime, levofloxacin, ciprofloxacin, meropenem, and tobramycin, all agents that are hydrophilic or relatively hydrophilic and against which the intact OM is not an effective permeability barrier.

TABLE 7

Sensitization factors* to selected antibacterial agents at NAB 7061 concentration of 4 μg/ml

| | E. coli ATCC 25922 | E. coli IH 3080 | K. pneum. ATCC 13883 | E. cloacae ATCC 23355 |
|---|---|---|---|---|
| Rifampin** | 250-750 | 170-350 | 250-500 | 750-1500 |
| Clarithromycin*** | 170-380 | 190-260 | 63 | 85-380 |
| Mupirocin*** | 64-170 | 64-85 | 24-32 | 250-512 |
| Azithromycin*** | 24-64 | 31-94 | 31-43 | 32 |
| Erythromycin*** | 32-48 | 32-42 | 24-48 | 21-43 |
| Fusidic acid | >43 | >43 | >4 | >8 |
| Quinupristin-dalfopr. | >21 | >21 | 1 | >5 |
| Clindamycin | 6 | 12 | 43 | 32 |
| Linezolid | >11 | >8 | >4 | >8 |
| Vancomycin | 5 | 2.5 | 1 | 32 |
| Polymyxin B | 5 | 2 | 1 | 4 |
| Trimetoprim | 4 | 3 | 2 | 3 |
| Moxifloxacin | 2.5 | 4 | 1.4 | 4 |

*Sensitization factor is the ratio of the MIC of the antibiotic in the absence of NAB 7061 to that in the presence of 4 μg/ml of NAB 7061
**Results from five independent determinations
***Results from two independent determinations

Example 8

Susceptibility of 33 Different Strains of Gram-Negative Bacteria to Rifampin and Clarithromycin in the Presence of NAB7061 (4 μg/ml)

The minimum inhibitory concentrations (MIC) of rifampin and clarithromycin for a representative set of different strains of clinically relevant Gram-negative bacteria were determined by the E-test method as in Example 7 and by using Mueller-Hinton agar with or without NAB7061 (4 μg/ml). This concentration of NAB7061 did not itself inhibit the growth of the target bacteria. The strains originated from ATCC (11 strains), CCUG (11 strains), and NCTC (The National Collection of Type Cultures, Colindale, U.K.; 2 strains). Eight strains (the F-strains) were purchased from Mobidiag Ltd., Helsinki, Finland. The source of E. coli IH3080 has been given in Example 2. Sensitization factor was defined as in Example 7.

The results are shown in Table 8. For all strains (17) belonging to the group consisting of E. coli, K. oxytoca, E. cloacae, and C. freundii, the MIC of rifampin was as low $\leq 0.125$ μg/ml in the presence of NAB7061 (4 μg/ml) and the sensitization factor varied from 85 to 2000. Very similar results were obtained with clarithromycin. For fifteen out of seventeen strains belonging to the group consisting of E. coli, K. oxytoca, E. cloacae, and C. freundii, the MIC of clarithromycin was as low as $\leq 0.25$ μg/ml in the presence of NAB7061 (4 μg/ml) and for all the 17 strains the sensitization factor varied from 90 to 1000. Strains of K. pneumoniae remained somewhat more resistant to both antibiotics, and the sensitization factors varied between 10 and 500. For the three strains of A. baumannii, the sensitization factors varied between 24 and 125, and the resulting MIC values were quite low (to rifampin $\leq 0.125$ μg/ml and to clarithromycin $\leq 0.5$ μg/ml).

TABLE 8

The ability of NAB 7061 to sensitize Gram-negative bacteria to model antibiotics (rifampin and clarithromycin)

| Bacterial strain | MIC (μg/ml) of rifampin in the presence of 4 μg/ml of NAB 7061* | Sensitization factor** to rifampin | MIC (μg/ml) of clarithromycin in the presence of 4 μg/ml of NAB 7061 | Sensitization factor*** to clarithromycin |
|---|---|---|---|---|
| E. coli ATCC25922**** | 0.016-0.047 | 250-750 | 0.094-0.125 | 170-400 |
| E. coli IH3080**** | 0.023-0.047 | 170-350 | 0.047-0.064 | 190-260 |
| E. coli CCUG41421 | 0.032-0.064 | 125 | 0.125 | 400 |
| E. coli CCUG41422 | 0.094-0.125 | 170-256 | 0.25 | 100 |
| E. coli CCUG41424 | 0.064-0.094 | 85-94 | 0.125 | 130 |
| E. coli CCUG41425 | 0.016-0.023 | 200-260 | 0.047 | 340 |
| E. coli CCUG41427 | 0.032-0.064 | 100-250 | 0.064 | 250 |
| E. coli CCUG41429 | 0.032 | 125-250 | 0.064 | 250 |
| E. coli CCUG41432 | 0.032 | 180-250 | 0.064 | 90 |
| E. coli NCTC13351 | 0.032-0.047 | 340-500 | 0.032 | 750 |
| E. coli NCTC13353 | 0.064 | 125-250 | 1 | 260 |
| K. pneumoniae ATCC13883**** | 0.064-0.125 | 250-500 | 0.19 | 60 |
| K. pneumoniae CCUG45421 | 2-3 | 10-20 | 24 | 10 |
| K. pneumoniae F145 | 0.19-0.25 | 170 | 0.25 | 170 |
| K. pneumoniae F144 | 0.19 | >170 | 0.75 | 64 |
| K. pneumoniae F136 | 0.75 | >43 | 2 | 24 |
| K. oxytoca ATCC13182 | 0.032-0.047 | 680-750 | 0.25 | 260 |
| K. oxytoca CCUG51683 | 0.012-0.023 | 700-2000 | 0.19 | 250 |
| E. cloacae ATCC23355**** | 0.008-0.016 | 750-1500 | 0.25-0.75 | 90-400 |
| E. cloacae CCUG52947 | 0.032-0.047 | 500-1000 | 0.38 | 350 |
| E. cloacae F230 | 0.016-0.032 | 1500 | 0.047 | 1000 |
| E. cloacae F232 | 0.023 | 1400 | 0.094 | 500 |
| C. freundii ATCC8090 | 0.023-0.032 | 500-1000 | 0.125 | 250 |
| Ac. baumannii ATCC19606 | 0.094-0.125 | 24-32 | 0.5 | 50 |
| Ac. baumannii F263***** | 0.032-0.19 | 21-125 | 0.38 | 40 |
| Ac. baumannii F264 | 0.125 | 32 | 0.25 | 100 |
| S. maltophilia ATCC17444 | 2 | 4-8 | 64 | 4 |
| S. marcescens ATCC8100 | 16 | <2 | 96 | <2 |
| P. mirabilis ATCC29906 | 1-6 | <2 | 24 | <2 |
| P. vulgaris ATCC13315 | 1-1.5 | <2 | 24 | <2 |
| P. aeruginosa ATCC27853 | 12-16 | 2 | 32 | <2 |

TABLE 8-continued

The ability of NAB 7061 to sensitize Gram-negative bacteria
to model antibiotics (rifampin and clarithromycin)

| Bacterial strain | MIC (μg/ml) of rifampin in the presence of 4 μg/ml of NAB 7061* | Sensitization factor** to rifampin | MIC (μg/ml) of clarithromycin in the presence of 4 μg/ml of NAB 7061 | Sensitization factor*** to clarithromycin |
|---|---|---|---|---|
| P. aeruginosa CCUG51971 | >32 | <2 | 64 | <2 |
| P. aeruginosa F58 | >32 | <2 | 256 | <2 |

*Results from two independent determinations
**Sensitization factor is the ratio of rifampin MIC in the absence of NAB 7061 to that in the presence of 4 μg/ml of NAB 7061
***Sensitization factor is the ratio of clarithromycin MIC in the absence of NAB 7061 to that in the presence of 4 μg/ml of NAB 7061
****Results from five (rifampin) and two (clarithromycin) independent determinations
*****Results from three independent determinations (rifampin)

Example 9

NAB7061 Sensitizes Carbapenem-Resistant Strains of Acinetobacter to Carbapenems

The minimum inhibitory concentrations (MIC) of two carpapenems, imipenem and meropenem, for three strains of A. baumannii were determined by the E-test method as in Example 7 and by using Mueller-Hinton agar with or without NAB7061 (4 μg/ml). This concentration of NAB7061 did not itself inhibit the growth of the target bacteria. Sensitization factor was defined as in Example 7. The results are shown in Table 9. NAB7061 sensitized both carbapenem-resistant strains (F263, F264) to both carbapenems by a factor ≧4.

TABLE 9

Antibacterial activity of imipenem and meropenem against Acinetobacter baumannii strains
in the absence of NAB 7061 and in the presence of NAB 7061 (4 μg/ml)

| Strain | MIC (μg/ml) of imipenem at the indicated concn (μg/ml) of NAB 7061 | | MIC (μg/ml) of meropenem at the indicated concn (μg/ml) of NAB 7061 | |
|---|---|---|---|---|
| | 0 | 4 | 0 | 4 |
| A. baumannii ATCC19606 | 0.38 | 0.38 | 1.5 | 0.75 |
| A. baumannii F263 | >32 | 8 | >32 | 6 |
| A. baumannii F264 | 24 | 6 | 32 | 4 |

Example 10

NAB7061 Sensitizes E. Coli to the Complement in Fresh Normal Serum

The ability of NAB7061 to sensitize encapsulated, smooth strain of E. coli to the bactericidal action of normal guinea pig serum (GPS) was studied by the method described by Vaara et al. (1984). E. coli IH3080 (O18,K1) was grown in LB broth (LB broth Lennox, Difco, BD, Sparks, Md., U.S.A) at 37° C. in a rotary shaker into early logarithmic growth phase, washed with PBS (phosphate-buffered saline, 8.0 g of NaCl, 0.2 g of KCl, 1.44 g of Na$_2$HPO$_4$×2H$_2$O and 0.2 g of KH$_2$PO$_4$ per liter) and resuspended in PBS, to approx. $10^9$ cells/ml). GPS was used as complement source. It was stored at −70° C. before use. To inactive the complement, serum was incubated at 56° C. for 30 min.

The experimental procedure was as follows. 10% GPS in PBS was inoculated with approx. 500 CFU (colony forming units) of bacteria per ml and pipetted in 0.2 ml aliquots into wells of microtiter plates. The wells already contained increasing amounts of NAB7061 in 0.020 ml of 0.9% NaCl. The plate was incubated at 37° C. for 2 h whereafter each well was emptied onto LB plates. The plates were incubated overnight at 37° C. and the developed colonies were counted.

The results are shown in Table 10. NAB7061 itself did not significantly reduce CFU count in the absence of GPS or in the presence of heat-inactivated 10% GPS. However, as low a concentration of NAB7061 as 2 μg/ml was sufficient to reduce CFU count by a factor of approx. 100 in the presence 10% fresh GPS. Accordingly, NAB7061 acts synergistically with the bactericidal complement machinery present in fresh serum, as does PMBN, the agent well known to have this property.

TABLE 10

The synergistic bactericidal activity of NAB7061 and 10%
guinea pig serum (GPS) against E. coli IH3080 (O18: K1)*

| | Concentration of NAB7061 (μg/ml) | | | |
|---|---|---|---|---|
| | 0 | 1 | 2 | 4 |
| none (PBS) | 100 | 97 | 97 | 79 |
| 10% GPS | 270 | 230 | 2 | 0 |
| 10% GPS, heat inactivated | 500 | 500 | 500 | 250 |

*measured as % survival after 2-hour treatment at 37° C.

Example 11

Reduced Affinity of NAB7061 to the Brush-Border Membrane (BBM) of the Renal Cortex The binding of the compounds according to this invention to isolated brush-border membrane (BBM) from the renal cortex can be measured indirectly by measuring their ability to inhibit the binding of radiolabelled gentamycin to BBM. Accordingly, the compounds according to this invention that have less affinity to BBM than for example polymyxin B inhibit the binding of radiolabelled gentamycin to a lesser degree than does polymyxin B.

BBM was isolated from the renal cortex of male albino rats by using the $Mg^{2+}$/EGTA precipitation technique as described by Nagai et al. (2006). The binding of gentamycin was measured, according to the method described by Nagai et al. (2006) by incubating BBM vesicles (20 µl) in 10 mM HEPES (pH 7.5) with 300 mM mannitol in the presence of 20 µM [$^3$H] gentamycin (American Radiolabeled Chemicals, Inc. (St. Louis, Mo., U.S.A.) with or without the compound to be tested or a positive control. After an incubation of 60 min at 4° C., 1 ml of ice-cold buffer described above was added, and the mixture was filtered through a Millipore filter (0.45 µm; HAWP). The filter was washed with the buffer and the radioactivity remaining in the filter was measured by using a liquid scintillation counter. The $IC_{50}$ values were determined as in Nagai et al. (2006) using the Hill equation.

The $IC_{50}$ values (µM) for the NAB compound studied and the controls were the following: 187.3±24.3 for NAB7061 (average of two independent experiments, each with three parallel determinations), 39.3±5.5 for polymyxin B (average of two independent experiments, each with three parallel determinations), and 90.2±9.7 for unlabelled gentamycin (three parallel determinations). Accordingly, the affinity of NAB7061 to BBM is only approximately half of the affinity of gentamycin to BBM and approximately one fifth of the affinity of polymyxin B to BBM. For NAB739 and NAB 740 the $IC_{50}$ values were 264±91 and 198±49. Therefore it can be concluded that the affinity of NAB739 to BBM is only approximately one sixth or seventh of the affinity of polymyxin B to BBM.

Example 12

The Activity of NAB7061 in Experimental *E. Coli* Peritonitis Model in Mice

A suspension of *E. coli* IH3080 (K1:O18) in saline (0.9% NaCl) was prepared from an overnight culture on a blood agar plate (Statens Serum Institut, Copenhagen, Denmark). All mice (female NMR1 from Harlan Scandinavia, Allerød, Denmark; weight, 25-30 g) were inoculated intraperitoneally with 0.5 ml of the suspension containing 0.96×10$^6$ CFU per ml in the lateral lower quadrant of the abdomen. At 1 h, the CFU count was determined from three mice and the remaining mice (four mice per group) were treated with a subcutaneous injection of 0.2 ml of erythromycin solution in saline (corresponding to 5 mg/kg body weight) or NAB7061 solution in saline (corresponding to 5 mg/kg body weight), or both erythromycin and NAB7061 (corresponding to 5 mg/kg body weight of both drugs; given at two separate sites). Control group received two 0.2 ml injections of saline. At 4.5 h postinfection, all mice were anaesthetized with $CO_2$ and sacrificed. Sterile saline (2 ml) was injected intraperitoneally and the abdomen was gently massaged before it was opened and the fluid sampled. Appropriate dilutions of the fluid were plated on blood agar plates, the plates were incubated overnight, and the colonies were counted.

At 1 h postinfection, the CFU count was 0.74 (±0.7)×10$^6$ per ml. At 4.5 h postinfection (corresponding to 3.5 h after the treatment), the CFU counts (per ml) were 11.1 (±6.2)×10$^6$ (control group), 8.9 (±6.4)×10$^6$ (erythromycin group), 1.1 (±0.6)×10$^6$ (NAB 7061 group), and 2.1 (±1.2)×10$^6$ (NAB plus erythromycin group). Accordingly, in the absence of NAB 7061, the bacterial count increased by a factor of 15 (saline group) or by a factor of 12 (erythromycin group), while in the presence of NAB 7061, the corresponding factors ranged from 1.5 to 3.

Example 13

Toxicity studies on NAB7061

Toxicity in young rats (weighing approx. 150 g in the beginning of the study) was determined by administering doses (1, 2, 4, 8, 16, and 32 mg/kg per day) of NAB7061 as well as the control compound polymyxin B intravenously twice (2) a day for two weeks. A group of ten (10) rats was studied for each dosage regimen. Clinical observations were made daily, the body weight measured twice weekly, and the food consumption twice weekly. In the end of week 2, all animals were sacrificed.

The control compound, polymyxin B negatively influenced the body weight gain at as low a dose as 1 mg/kg per day whereas the lowest dose of NAB7061 that had this effect was 8 mg/kg. Polymyxin B caused mortality at 32 mg/kg per day (100% mortality), whereas all rats receiving NAB7061 remained alive throughout the study. In the end of the study, blood urea nitrogen (BUN) was 15% higher in the group receiving polymyxin 16 mg/kg per day than in the control or low dose polymyxin group (1 mg/kg per day). In the group that received NAB7061 at the dose of 16 mg/kg per day, no such a rise was found, and in the group that received NAB7061 at the dose of 32 mg/kg per day, the rise was 7%.

Histopathology of kidneys was performed for each animals and histopathology of all tissues was performed in three high-dose groups receiving NAB7061. No NAB7061-related pathological findings were found in the general pathology and histopathology of any organs or in the histopathology of kidneys in any animals that received NAB7061.

Example 14

Preparation and Biological Activity of NAB 739 Methanesulfonate Sodium Salt

NAB 739 acetate (100 mg) was dissolved in water (2 ml) and neutral formaldehyde solution (400 microliters of 30% aqueous formaldehyde [brought to pH 7.2 with 1 N Na—$HCO_3$]) was added. Then, 1 N $NaHCO_3$ solution (2 ml) was added, and the precipitated NAB 739 formaldehyde derivative was filtered and washed with water. The moist solid was suspended in water (5 ml), and sodium metabisulphite (100 mg) was added. A clear solution was obtained after a few minutes and was freeze-dried. The flocculent white solid was extracted with warm acetone (7.5 ml) and dried in vacuo. The yield was 56 mg. Analysis of the product by ESI mass spectrometry revealed a predominant peak with the molecular mass of 1075.3 indicating that most of the derivative was sulfomethylated at each of the three Dab residues of the NAB 739 compound. A minor peak representing the NAB 739 blocked randomly at two of the three Dab residues was also visible.

For the measurement of the antibacterial activity of aqueous solutions of NAB 739 methanesulfonate sodium, three different solutions were made: 1) A solution (1 mg/ml) made in 0.9% NaCl immediately prior to the experiment, 2) a solution (1 mg/ml) made in 0.9% NaCl 24 h prior to the experiment and kept at 37° C., 3) a solution (1 mg/ml) made in 0.9% NaCl 48 h prior to the experiment and kept at 37° C. A freshly made solution of NAB 739 acetate served as the control compound.

TABLE 11

The bactericidal activity of NAB 739 methanesulfonate as compared with that of NAB 739 against *E. coli* IH3080*

| Compound | Solution age | Concentration of the compound (μg/ml) | | | |
|---|---|---|---|---|---|
| | | 0 | 1 | 2 | 4 |
| NAB 739 MS** | fresh | 100 | 70 | 62 | 16 |
| NAB 739 MS** | 24 h | | 55 | 34 | 6 |
| NAB 739 MS** | 48 h | | 35 | 11 | 0 |
| NAB 739 | fresh | | 21 | 2 | 0 |

*measured as % survival after 2-hour treatment at 37 degrees centigrade.
**MS, methanesulfonate The test bacterium was *E. coli* IH3080. It was grown in LB broth (LB broth Lennox, Difco, BD, Sparks, Md., U.S.A.) at 37 Celsius in a rotary shaker into early logarithmic growth phase, washed with PBS, and resuspended in PBS to approx. 10e9 cells/ml. PBS was inoculated with approx. 500 CFU (colony forming units) of bacteria per ml and pipetted in 0.2 ml aliquots into wells of a microtiter plate. The plates already contained increasing concentrations of NAB 739 methanesulfonate or the control compound in 0.020 ml of 0.9% NaCl. The plate was incubated at 37° C. for 1 h whereafter each well was emptied onto LB plates. The plate was incubated overnight at 37° C. and the developed colonies were counted.

The results are shown in Table 11. The fresh solution of NAB 739 methanesulfonate was much less antibacterial than the control compound NAB 739. Keeping the NAB 739 methanesulfonate solution at 37° C. for 24 h prior to use slightly increased the activity whereas keeping for 48 h resulted in activity almost equal to that observed with the control compound. These results indicate that NAB 739 methanesulfonate, in analogy with colistin methanesulfonate, slowly decomposes in aqueous solutions to yield antibacterially more active substances, i.e., less sulfomethylated substances and eventually free NAB 739.

Example 15

Minimum inhibitory concentrations of NAB739, NAB740 and NAB7061 for 38 strains of Gram-negative bacteria The MIC values of NAB 739, NAB 740, and NAB7061 were determined by using the agar dilution method according to the CLSI protocol M7-A7. Polymyxin B sulfate (Sigma-Aldrich, St. Louis, Mo., USA) was used as a control. Mueller Hinton agar (Difco 225220, BD, Sparks, Md., U.S.A.) plates containing increasing concentrations (from 0.25 to 32 μg/ml; two-fold increments) of the test substances were used. The bacterial test strains originated from ATCC (10 strains), CCUG (11 strains), and NCTC (3 strains). Fourteen (14) strains (the F-strains) were purchased from Mobidiag Ltd., Helsinki, Finland. Besides bacteria, the MIC was also determined for the yeast *Candida albicans* (ATCC 28366 from ATCC).

The inocula were prepared by adjusting the bacterial suspensions to a density equivalent to $OD_{546\,nm}$~0.3 (~$10^8$ CFU/ml~0.5 McFarland) the yeast suspension to a density equivalent to $OD_{546\,nm}$~0.75 (~$2\times10^7$ CFU/ml). The suspensions were diluted to $10^7$ CFU/ml. The plates were inoculated by using a Denley Multipoint Inoculator, 1 μl per spot corresponding to approx. $10^4$ CFU/spot. Plates were incubated for 16-20 hours at 35° C.

Table 12 shows the results. The MIC values of NAB 739 for *E. coli* strains ranged from 0.5 to 1 μg/ml and those of NAB740 from 1 to 2 μg/ml. Both agents had good activity also against other polymyxin-susceptible strains of Enterobacteriaceae. The MIC of NAB 740 for *Pseudomonas aeruginosa* ranged from 4 to 8 μg/ml. *S. aureus* and *C. albicans* were resistant to the NAB peptides.

TABLE 12

MIC values (μg/ml) of NAB 739, NAB 740, NAB 7061, and polymyxin B for Gram-negative strains as well as for *Staphylococcus aureus* and *Candida albicans*.

| | NAB 739 | NAB 740 | NAB 7061 | Polym. B |
|---|---|---|---|---|
| *E. coli* ATCC 25922 | 1 | 2 | >32 | 1 |
| *E. coli* IH3080 | 1 | 2 | >32 | 0.5 |
| *E. coli* CCUG 41421 | 1 | 2 | >32 | 0.5 |
| *E. coli* CCUG 41422 | 1 | 2 | >32 | 1 |
| *E. coli* CCUG 41424 | 1 | 2 | 32 | 1 |
| *E. coli* CCUG 41425 | 1 | 2 | >32 | 0.5 |
| *E. coli* CCUG 41427 | 1 | 1 | >32 | 1 |
| *E. coli* CCUG 41429 | 1 | 1 | 16 | 1 |
| *E. coli* CCUG 41432 | 1 | 2 | >32 | 1 |
| *E. coli* NCTC 13351 | 0.5 | 1 | >32 | 0.5 |
| *E. coli* NCTC 13352 | 1 | 1 | 32 | 0.25 |
| *E. coli* NCTC 13353 | 1 | 2 | >32 | 1 |
| *E. coli* F8 | 1 | 2 | >32 | 1 |
| *E. coli* F9 | 1 | 2 | >32 | 0.5 |
| *E. coli* F10 | 1 | 2 | >32 | 0.5 |
| *E. coli* F18 | 1 | 2 | >32 | 0.5 |
| *E. coli* F19 | 0.5 | 1 | 32 | 1 |
| *K. pneumoniae* ATCC 13883 | 32(-2/4) | 8 | >32 | 32(-8) |
| *K. pneumoniae* CCUG 45421 | 4 | 4 | >32 | 1 |
| *K. pneumoniae* F136 | 1 | 2 | >32 | 0.5 |
| *K. pneumoniae* F144 | 2 | 16(-4) | >32 | 1 |
| *K. pneumoniae* F145 | 2 | 2 | >32 | 0.5 |
| *K. oxytoca* ATCC 13182 | 2 | 2 | 32 | 0.5 |
| *K. oxytoca* CCUG 51683 | 2 | 2 | 32 | 0.5 |
| *E. cloacae* ATCC 23355 | 2 | 2 | 32 | 0.5 |
| *E. cloacae* CCUG 52947 | 2 | 2 | >32 | 1 |
| *E. cloacae* F230 | 2 | 2 | >32 | 0.5 |
| *E. cloacae* F231 | 2 | 2 | 32 | 0.5 |
| *E. cloacae* F232 | 2 | 2 | >32 | 0.5 |
| *C. freundii* ATCC 8090 | 2 | 2 | 16 | 1 |
| *A. baumannii* ATCC 19606 | 8 | 4 | >32 | 1 |
| *A. baumannii* F263 | 4 | 2 | >32 | 1 |
| *A. baumannii* F264 | 4 | 2 | >32 | 0.5 |
| *S. maltophilia* ATCC 17444 | 16 | 8 | >32 | 1 |
| *S. marcescens* ATCC 8100 | >32 | >32 | >32 | >32 |
| *P. aeruginosa* ATCC 27853 | 8 | 4 | >32 | 1 |
| *P. aeruginosa* CCUG 51971 | 8 | 8 | >32 | 2 |
| *P. aeruginosa* F58 | 8 | 4 | >32 | 0.5 |
| *S. aureus* ATCC 25923 | >32 | >32 | >32 | >32 |
| *C. albicans* ATCC 28366 | >32 | >32 | >32 | >32 |

Example 16

The Effect of Subinhibitory Concentrations of NAB739 on the Susceptibility of *A. baumannii* and *P. aeruginosa* to Antibacterial Agents The MIC values of six antibacterial agents were determined for two strains of *A. baumannii* (ATCC 19606 and F264) and for *P. aeruginosa* ATCC27853 by the E-test method as described in Example 7 and by using Mueller Hinton agar medium (product no Labo39; LabM Ltd., Bury, Lancs, U.K.) containing increasing concentrations of NAB739.

The results are shown in Table 13. NAB739 sensitized at as low a concentration as 0.5 μg/ml both *Acinetobacter* strains to rifampin (sensitization factors, 85-128), chlarithomycin (sensitization factors, 12-16), fusidic acid (sensitization factors, 64-85), and vancomycin (sensitization factor, 85). The MIC of vancomycin for both strains was as low as 3 μg/ml in the presence of NAB739 at 0.5 μg/ml. The strain F264 was resistant to meropenem, but in the presence of NAB 739 (0.5

μg/ml) the MIC of meropenem was as low as 1 μg/ml. NAB739 had a modest effect on the MIC values of rifampin and chlarithomycin for *P. aeruginosa*.

TABLE 13

The MICs (μg/ml) of five antibiotics for *A baumannii*, and *P. aeruginosa* in the presence of NAB739

| Bacterial strain | Antibiotic | Concentration (μg/ml) of NAB 739 (μg/ml) | | | | | |
|---|---|---|---|---|---|---|---|
| | | 0 | 0.125 | 0.25 | 0.5 | 1 | 2 |
| *A. baumannii* ATCC19606 | Clarithromycin | 8 | 1.5 | 1 | 0.5 | 0.094 | NA |
| | Rifampicin | 4 | 0.25 | 0.125 | 0.047 | 0.006 | NA |
| | Vancomycin | >256 | 64 | 8 | 3 | 1 | NA |
| | Fusidic acid | >256 | 32 | 12 | 4 | 1 | NA |
| | Meropenem | 1 | 1 | 0.5 | 0.25 | 0.125 | NA |
| *A. baumannii* F264 | Clarithromycin | 6 | 2 | 1.5 | 0.5 | 0.125 | NA |
| | Rifampicin | 12 | 0.5 | 0.38 | 0.094 | 0.016 | NA |
| | Vancomycin | >256 | 256 | 16 | 3 | 1 | NA |
| | Fusidic acid | >256 | 32 | 12 | 3 | 1 | NA |
| | Meropenem | >32 | 32 | 6 | 1 | 0.38 | NA |
| *P. aeruginosa* ATCC 27853 | Clarithromycin | 48 | 32 | 32 | 16 | 12 | 3 |
| | Rifampicin | 32 | 32 | 32 | 32 | 16 | 4 |
| | Vancomycin | >256 | >256 | >256 | >256 | >256 | >256 |
| | Fusidic acid | >256 | >256 | >256 | >256 | >256 | 192 |
| | Meropenem | 0.25 | 0.25 | 0.25 | 0.25 | 0.25 | 0.25 |

* NA, not applicable, NAB 739 alone inhibited the growth

Example 17

The Synergistic Effect of NAB7061 and Erythromycin in Experimental *E. coli* Peritonitis Model in Mice The experiment was performed by using the methodology described in Example 12.

The mice were inoculated intraperitoneally with 0.5 ml of the *E. coli* IH3080 suspension containing $6.5 \times 10^5$ CFU per ml. The treatment groups (8 animals per group) were the following: A, control animals receiving saline; B, animals receiving erythromycin (20 mg/kg) intraperitoneally at 1 h postinfection; C, animals receiving NAB7061 (5 mg/kg) subcutaneously at 1 h postinfection, followed at 3 h postinfection by another dose of NAB7061 (5 mg/kg) subcutaneously; D, animals receiving erythromycin (20 mg/kg) intraperitoneally and NAB7061 (5 mg/kg) subcutaneously at 1 h postinfection, followed at 3 h postinfection by another dose of NAB7061 (5 mg/kg) subcutaneously.

The CFU counts from the peritoneum from four animals of each group at 4 h postinfection and at 7 h postinfection were determined. At 4 h postinfection, the CFU counts in the group D (NAB7061+erythromycin) was $\geq 100$-fold lower and at 7 h postinfection $\geq 1000$-fold lower than the counts in the other groups (A, B, C). This indicates that the combination of NAB7061 and a model antibiotic acted very effectively.

Example 18

The Effect of NAB739 in Experimental *E. Coli* Peritonitis Model in Mice

The experiment was performed by using the methodology described in Example 12.

The mice were inoculated intraperitoneally with 0.5 ml of the *E. coli* IH3080 suspension containing $1 \times 10^6$ CFU per ml. The treatment groups (7 animals per group) were the following: A, control animals receiving saline; B, animals receiving the dose of 1 mg/kg of NAB739 subcutanously at 1 h and at 3 h postinfection; C, animals receiving the dose of 2 mg/kg of NAB739 subcutanously at 1 h and at 3 h postinfection; D, animals receiving the dose of 4 mg/kg of NAB739 subcutanously at 1 h and at 3 h postinfection; E, animals receiving the dose of 2 mg/kg of the control compound, polymyxin B sulfate (Sigma-Aldrich, P0972) subcutaneously at 1 h and at 3 h postinfection.

The CFU counts from the peritoneum from four animals of each group at 4 h postinfection and from three animals of each group at 7 h postinfection were determined. At both 4 h and 7 h postinfection, the CFU counts in the groups C (NAB739, 2 mg/kg) and D (NAB739, 4 mg/kg) were $\geq 10\,000$-fold lower (i.e. $\geq 4$ log 10 lower) than those in the saline control group (group A). Even the NAB739 dose 1 mg/kg was very effective, since at 7 h postinfection the CFU counts in the group B (NAB739, 1 mg/kg) was $\geq 10\,000$-fold lower than those in the saline control group (group A). These results indicate that NAB739 is a very effective agent in the therapy of experimental murine peritonitis.

Example 19

Basic Pharmakokinetic Evaluation of NAB 7061

The study was principally performed by using the methods described by Li et al. (2003, 2004). Each rat (n=5, Sprague-Dawley, male) was anaesthetized using isoflurane, and a polyethylene cannula was inserted into the jugular vein. Each rat was placed into a metabolic cage and allowed to recover from the procedure overnight. NAB 7061 (acetate, 1 mg/kg) was administered as a bolus (in 200 μl sterile 0.9% saline) through the cannula, followed by washing with 0.8 ml of saline. Nine blood samples (0, 10, 20, 30, 60, 90, 120, 180, and 240 min), each 200 μl, were manually collected through the cannula. When collecting samples, the first 100 μl of blood was withdrawn and kept in the syringe. After collecting the actual sample with another syringe, the content of the first syringe was returned to the rat together with 400 μl of heparinized saline. Blood samples were centrifuged to obtain plasma. Urine samples were collected in 0-4 h, 4-6 h, and 6-24 h intervals. Plasma and urine samples were stored at −80° C.

To a 100-μl sample, 100 μl of acetonitrile was added, the mixture was vortex-mixed for 1 min, and centrifuged at 10,000 g for 10 min. The supernatant was transferred to an SPE C18 cartridge (Sep-Pak, Waters, Mass. USA) for derivatization with 9-fluorenylmethyl chloroformate. The derivatization was according to the method previously described by Li et al. (2001) for the assay of colistin. The chromatography employed the HPLC C18 column (50×4.6 mm), the mobile phase of acetonitrile/tetrahydrofuran/water (60:15:30, v/v), the flow rate of 1.0 ml/min, and the detection at an excitation wavelength of 260 nm and an emission wavelength of 315 nm. The retention time of NAB 7061 was approximately 4.3 min. Non-compartmental analysis of NAB 7061 in plasma was performed using PK Functions for Microsoft Excel (Allergan, Irvine, Calif., USA).

The basic pharmacokinetic parameters determined for NAB 7061 were as follows: half-life (min), 66.2±12.3; volume of distribution (ml/kg), 339±96; clearance (ml/min/kg), 3.84±0.75; urinary recovery (% of dose in 24 h), 7.16±3.70; and renal clearance (ml/min/kg), 0.28±0.16.

The corresponding parameters for colistin, as determined by Li et al. (2003) by using an identical dosing and administration procedure, are the following: half-life (min), 74.6±13.2; volume of distribution (ml/kg), 496±60; clearance (ml/min/kg), 5.2±0.4; urinary recovery (% of dose in 24 h), 0.18±0.14; and renal clearance (ml/min/kg), 0.010±0.008.

Example 20

Basic Pharmakokinetic Evaluation of NAB 739

The dosing and administration of NAB 739 was performed by using the method described by Li et al. (2003, 2004) and was essentially the same as that described for NAB 7061 in the Example 19. Four rats (Sprague-Dawley, male) were studied. NAB 739 (acetate, 1 mg/kg) was administered as a bolus (in 200 µl sterile 0.9% saline) through the cannula.

The samples were analyzed using liquid chromatography and mass spectrometry with electrospray ionization interface (LC/electrospray ionization MS). To a 100-µl sample, 10 µl of internal standard (NAB 741, 80 µg/ml) and 200 µl (plasma samples) or 100 µl (urine samples) of acetonitrile was added, the mixture was vortex-mixed for 1 min, and centrifuged at 10,000 g for 10 min. The chromatography employed the HPLC C18 column (50×2 mm), 0.1% formic acid as the solvent A, 0.1% acetonitrile as the solvent B, flow rate of 0.2 ml/min, and the following gradient: 5%-30% B in 6 min, 30%-90% B in 0.5 min, 90% B held for 2.7 min, 90%-5% B in 1 min. The eluent between 5.90-7.00 min and 9.00-10.1 min was directed to the MS system using a switching valve. The positive protonated molecular ions of NAB 739 at m/z=538.8 and 359.6 and NAB 741 at m/z 496.7 and 331.4 were monitored. NAB 739 and NAB 741 eluted at 9.50±0.03 and 6.60±0.06 min, respectively. Non-compartmental analysis of NAB 739 in plasma was performed using WinNonlin software (version 4.0, Mountain View, Calif., USA), with the model of NA201 (i.v. bolus input for plasma data).

The basic pharmacokinetic parameters determined for NAB 739, were as follows: half-life (min), 69.0±21.9; volume of distribution (ml/kg), 222±20.5; clearance (ml/min/kg), 2.63±0.54; urinary recovery (% of dose in 24 h), 19.4±7.38; and renal clearance (ml/min/kg), 0.53±0.30.

The corresponding parameters for colistin, as determined by Li et al. (2003) by using an identical dosing and administration procedure, are the following: half-life (min), 74.6±13.2; volume of distribution (ml/kg), 496±60; clearance (ml/min/kg), 5.2±0.4; urinary recovery (% of dose in 24 h), 0.18±0.14; and renal clearance (ml/min/kg), 0.010±0.008.

The invention claimed is:

1. A polymyxin derivative of formula:

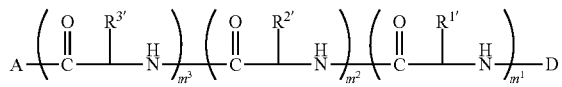

wherein A is a polymyxin ring moiety, wherein the polymyxin ring moiety has a formula of

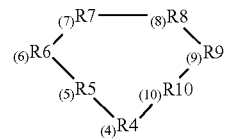

wherein
R$^{1'}$ is the side chain of Abu;
R$^{2'}$ is the side chain of Ala, Abu, Asn, Asp, Glu, Gln, Ser or Thr, each of which may be in the L or D configuration;
R$^{3'}$ is the side chain of Ala, Abu, Asn, Asp, Glu, Gln, Ser or Thr, each of which may be in the L or D configuration;
R4 is Glu, Asp, Dab, diaminopropionic acid, Thr, Ser or Cys;
R5 is Dab or Abu;
R6 is D-Phe or D-Leu;
R7 is Leu, Thr or Ile;
R8 is Dab or Abu;
R9 is Dab or Abu;
R10 is Thr or Leu;
m$^1$ is 0 or 1;
m$^2$ and m$^3$ are each 1;
D is selected from R$^{12}$—(C=O)—, R$^{12}$—SO$_2$—; R$^{12}$—(C=NH)—; R$^{12}$—NH—(C=S)—; R$^{12}$—NH—(C=O)—; R$^{12}$—NH—(C=NH)—; R$^{12}$—O—(C=S)—; R$^{12}$—O—(C=O)—; R$^{12}$—P(O)OH—; R$^{12}$—(C=S)—; or R$^{12}$—, wherein R$^{12}$ is optionally substituted alkyl, alkenyl, alkynyl, aryl or aryl alkyl;
wherein said polymyxin derivative has at least two but no more than three positive charges at physiological pH.

2. The polymyxin derivative claim 1, wherein m$^1$ is 0.

3. The polymyxin derivative of claim 1,
wherein R4 is Dab, R5 is Dab, R6 is D-Phe, R7 is Leu, R8 is Dab, R9 is Dab, and R10 is Thr; or
wherein R4 is Dab, R5 is Dab, R6 is D-Leu, R7 is Leu, R8 is Dab, R9 is Dab, and R10 is Thr.

4. The polymyxin derivative of claim 1, wherein D is octanoyl, nonanoyl, isononanoyl, decanoyl, isodecanoyl, undecanoyl, dodecanoyl, tetradecanoyl, cyclohexyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl, heptanoyl, or 9-fluorenylmethoxycarbonyl.

5. A polymyxin derivative of formula:

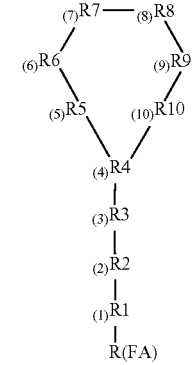

wherein
R1 is Abu or is absent;
R2 is Ala, Abu, Asn, Asp, Glu, Gln, Ser or Thr, each of which may be in the L or D configuration;

R3 is Ala, Abu, Asn, Asp, Glu, Gln, Ser or Thr, each of which may be in the L or D configuration;

R4 is Glu, Asp, Dab, diaminopropionic acid, Thr, Ser or Cys;

R5 is Dab or Abu;

R6 is D-Phe or D-Leu;

R7 is Leu, Thr or Ile;

R8 is Dab or Abu;

R9 is Dab or Abu;

R10 is Thr or Leu;

R(FA) is octanoyl, nonanoyl, isononanoyl, decanoyl, isodecanoyl, undecanoyl, dodecanoyl, tetradecanoyl, cyclohexyl, cycloheptanoyl, cyclooctanoyl, cyclononanoyl, cycloisononanoyl, cyclodecanoyl, cycloisodecanoyl, cycloundecanoyl, cyclododecanoyl, cyclotetradecanoyl, hexanoyl, heptanoyl, or 9-fluorenylmethoxycarbonyl;

wherein said polymyxin derivative has at least two but no more than three positive charges at physiological pH.

6. A combination product comprising two or more of the polymyxin derivatives according to claim 1.

7. A pharmaceutical composition comprising at least one polymyxin derivative according to claim 1, and at least one pharmaceutically acceptable carrier and/or excipient.

8. The pharmaceutical composition according to claim 7, further comprising a second antibacterial agent.

9. A method for sensitizing Gram-negative bacteria to an antibacterial agent, comprising administering, simultaneously or sequentially in any order, a therapeutically effective amount of said antibacterial agent and a polymyxin derivative according to claim 1 to a subject in need thereof.

10. A method for sensitizing clinically important Gram-negative bacteria to a host defense mechanism complement present in the serum, comprising administering to a subject in need thereof a polymyxin derivative according to claim 1 during a clinical infection.

11. A method for treating a Gram-negative bacterial infection in a subject, comprising administering an effective amount of a polymyxin derivative of claim 1 to said subject, such that said bacterial infection is treated.

12. A method for treating a Gram-negative bacterial infection in a subject, comprising administering an effective amount of a polymyxin derivative of claim 1 in combination with an antibacterial agent, such that the bacterial infection is treated.

13. The polymyxin derivative of claim 1, wherein said polymyxin derivative possesses antibacterial activity against Gram-negative bacteria, and/or possesses the ability to sensitize Gram-negative bacteria to antibacterial agents.

14. A composition comprising a polymyxin derivative of formula DA-cy[Dab-Dab-D-Phe-Leu-Dab-Dab-Thr-] (NAB-736), wherein DA is decanoyl.

15. A composition comprising a polymyxin derivative of formula OA-Thr-Thr-D-Ser-cy[Dab-Dab-D-Phe-Leu-Dab-Dab-Thr-] (NAB-748), wherein OA is octanoyl.

16. A composition comprising a polymyxin derivative of formula OA-Ala-Thr-D-Ser-cy[Dab-Dab-D-Phe-Leu-Dab-Dab-Thr-] (NAB-749), wherein OA is octanoyl.

* * * * *